United States Patent
Takaoka et al.

(10) Patent No.: US 10,288,592 B2
(45) Date of Patent: May 14, 2019

(54) FUNCTION DIAGNOSTIC SYSTEM FOR FILTER OF INTERNAL COMBUSTION ENGINE

(71) Applicant: TOYOTA JIDOSHA KABUSHIKI KAISHA, Toyota-shi, Aichi-ken (JP)

(72) Inventors: Kazuya Takaoka, Gotemba (JP); Toru Kidokoro, Hadano (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 202 days.

(21) Appl. No.: 14/962,210

(22) Filed: Dec. 8, 2015

(65) Prior Publication Data

US 2016/0161458 A1 Jun. 9, 2016

(30) Foreign Application Priority Data

Dec. 8, 2014 (JP) ................................. 2014-248435

(51) Int. Cl.
*F01N 3/035* (2006.01)
*G01N 33/00* (2006.01)
*F01N 3/20* (2006.01)

(52) U.S. Cl.
CPC ......... *G01N 33/0037* (2013.01); *F01N 3/035* (2013.01); *F01N 3/2066* (2013.01); *G01N 33/0029* (2013.01); *G01N 33/0073* (2013.01); *F01N 2550/04* (2013.01); *Y02T 10/24* (2013.01)

(58) Field of Classification Search
None
See application file for complete search history.

(56) References Cited

U.S. PATENT DOCUMENTS

| | | | |
|---|---|---|---|
| 2011/0320171 A1* | 12/2011 | Okayama | B01D 46/0086 702/183 |
| 2014/0230415 A1 | 8/2014 | Shimode et al. | |
| 2015/0226145 A1* | 8/2015 | Iwatani | F02D 41/025 60/285 |
| 2015/0315950 A1 | 11/2015 | Hagimoto | |
| 2016/0069241 A1 | 3/2016 | Takaoka | |

FOREIGN PATENT DOCUMENTS

| | | | | |
|---|---|---|---|---|
| JP | 2013-108452 A | 6/2013 | | |
| JP | 2016-056701 A | 4/2016 | | |
| WO | WO 2013/042190 A1 | 3/2013 | | |
| WO | WO-2014038550 A1 * | 3/2014 | ........... | F02D 41/025 |
| WO | WO 2014/087536 A1 | 6/2014 | | |

\* cited by examiner

*Primary Examiner* — Matthew D Krcha
(74) *Attorney, Agent, or Firm* — Finnegan, Henderson, Farabow, Garrett & Dunner, LLP

(57) ABSTRACT

A function diagnostic system for a filter of an internal combustion engine may be provided. The function diagnostic system may include a PM sensor and an electronic control unit. The electronic control unit may be configured to: calculate a NOx conversion rate in the filter; determine whether a NOx converting function of the filter is normal; execute a sensor regeneration process for removing the PM deposited between an electrodes of the PM sensor; continuously monitor an output value of the PM sensor after a predetermined PM deposition restart time, after execution of the sensor regeneration process is finished; and determine that there is an abnormality in a PM trapping function of the filter, when the output vale of the PM sensor, which has been continuously monitored, is reduced when the electronic control unit determines that the NOx converting function of the filter is in a normal status.

5 Claims, 12 Drawing Sheets

FUNCTION DIAGNOSTIC SYSTEM FOR FILTER OF INTERNAL COMBUSTION ENGINE

INCORPORATION BY REFERENCE

The disclosure of Japanese Patent Application No. 2014-248435 filed on Dec. 8, 2014 including the specification, drawings and abstract is incorporated herein by reference in its entirety.

BACKGROUND

1. Technical Field

The invention relates to a filter function diagnostic system for diagnosing the functions of a filter of internal combustion engine on which a selective reduction NOx catalyst is supported. This type of filter has a PM trapping function of trapping PM (Particulate Matter) in exhaust gas, and also has a NOx converting function of reducing NOx in exhaust gas, using ammonia as a reducing agent.

2. Background

A technology of providing a filter that traps PM in exhaust gas, in an exhaust passage of an internal combustion engine, is known. In some cases, a failure, such as erosion or breakage, occurs to the filter. If such a failure of the filter occurs, the amount of PM that flows out from the filter, without being trapped by the filter, is increased. If the failure occurs to the filter, or an abnormality, such as removal of the filter from the exhaust passage, arises in the filter, the PM released to the atmosphere is increased. Thus, a technology of providing a PM sensor in the exhaust passage downstream of the filter, and conducting an abnormality diagnosis on the filter based on the output value of the PM sensor has been developed. As one type of the PM sensor used for the abnormality diagnosis of the filter, a sensor that has a pair of electrodes as a sensor element, and outputs a signal corresponding to the amount of PM deposited between the electrodes, is known.

Also, an emission control system is known in which a filter, an aqueous urea addition device, a selective reduction NOx catalyst (which may be called "SCR catalyst"), and a PM sensor are arranged in this order from the upstream side along flow of exhaust gas, in the exhaust passage of the internal combustion engine. The SCR catalyst has a function of reducing NOx in exhaust gas, using ammonia produced by hydrolyzing urea injected from the aqueous urea addition device, as a reducing agent. In the emission control system constructed as described above, when the PM is detected by the PM sensor, injection of aqueous urea from the aqueous urea addition device is limited, as disclosed in International Publication No. 2013/042190

If the PM trapping function of the filter declines due to occurrence of a failure in the filter, the amount of PM flowing out from the filter is increased. Therefore, the amount of PM trapped between the electrodes of the PM sensor provided in the exhaust passage downstream of the filter is increased. As a result, the amount of PM deposited between the electrodes of the PM sensor becomes larger than that in the case where the filter is in a normal condition. Therefore, the PM trapping function of the filter can be diagnosed, based on the output value of the PM sensor obtained at a given time.

SUMMARY

In recent years, a filter on which the SCR catalyst is supported has been developed. As discussed in this disclosure, this type of filter may be called "SCRF". The SCRF has the PM trapping function of trapping PM in exhaust gas, and also has the NOx converting function of reducing NOx in exhaust gas, using ammonia as a reducing agent.

When the filter is in the form of the SCRF, aqueous urea is supplied to the SCRF from the upstream side, so that NOx contained in exhaust gas is reduced in the SCRF. If the aqueous urea thus supplied slips though the SCRF, and reaches the PM sensor, the aqueous urea may have an influence on the output value of the PM sensor. In this case, an erroneous diagnosis may be made if the PM trapping function of the SCRF is diagnosed by a diagnosing method similar to that as described above, based on the output value of the PM sensor provided in the exhaust passage downstream of the SCRF.

Disclosed embodiments may provide a filter function diagnostic system for diagnosing the PM trapping function of a SCRF, using the output value of a PM sensor provided in an exhaust passage downstream of the SCRF.

A function diagnostic system for a filter of an internal combustion engine according to disclosed embodiments may be provided. The filter may be provided in an exhaust passage of the internal combustion engine. The filter may be configured to support a selective reduction NOx catalyst that reduces NOx in exhaust gas, using ammonia as a reducing agent. The filter may be configured to trap PM contained in the exhaust gas. The internal combustion engine may include an aqueous urea addition device located upstream of the filter in the exhaust passage. The aqueous urea addition device may be configured to inject aqueous urea into the exhaust gas. The function diagnostic system may include a PM sensor and an ECU. The PM sensor may be provided downstream of the filter in the exhaust passage. The PM sensor may have a pair of electrodes. The PM sensor may be configured to output a signal corresponding to a deposition amount of the PM when the PM is deposited between the pair of electrodes and the pair of electrodes are electrically conducted. The ECU may be configured to: (i) calculate a NOx conversion rate in the filter, (ii) determine whether a NOx converting function of the filter is normal, based on the NOx conversion rate, (iii) execute a sensor regeneration process for removing the PM deposited between the electrodes of the PM sensor, (iv) continuously monitor an output value of the PM sensor after a predetermined PM deposition restart time, after execution of the sensor regeneration process is finished, the PM deposition restart time being a point in time at which deposition of the PM between the electrodes of the PM sensor is supposed to be restarted, and (v) determine that there is an abnormality in a PM trapping function of the filter, when the output vale of the PM sensor, which has been continuously monitored, is reduced when the electronic control unit determines that the NOx converting function of the filter is in a normal status.

In the function diagnostic system according to the above aspect of the disclosure, aqueous urea injected from the aqueous urea addition device into the exhaust gas may be supplied to the SCRF. Then, ammonia produced by hydrolyzing the aqueous urea supplied may be adsorbed on the SCR catalyst supported on the SCRF. In the SCRF, NOx in exhaust gas may be reduced, using the ammonia as a reducing agent. It was found that, even when a failure, such as breakage or erosion, occurs to the SCRF (namely, even when there is an abnormality in the PM trapping function), the NOx converting function of the SCRF may be in a normal status. It was also found that, if there is an abnormality in the PM trapping function of the SCRF, aqueous urea supplied to the SCRF may flow out from the SCRF even when its NOx converting function is in a normal status.

During a period in which trapped PM is deposited between the electrodes of the PM sensor, namely, after the PM deposition restart time, aqueous urea may be injected from the aqueous urea addition device. At this time, if the outflow of aqueous urea as described above takes place, the aqueous urea may be attached to between the electrodes of the PM sensor, and may have an influence on the output value of the PM sensor. Thus, the output value of the PM sensor may be continuously monitored after the predetermined PM deposition restart time as the time when deposition of PM between the electrodes of the PM sensor is supposed to be restarted, after completion of the sensor regeneration process. When a voltage is applied across the electrodes of the PM sensor after completion of the sensor regeneration process, the voltage application start time may be regarded as the PM deposition restart time. Also, when a voltage starts being applied to the electrodes of the PM sensor before completion of the sensor regeneration process, the time of completion of the sensor regeneration process may be regarded as the PM deposition restart time. In this case, a point in time at which a predetermined period it takes for the temperature of the electrodes of the PM sensor to be lowered to such a level that the trapped PM is not oxidized has elapsed from the time when the sensor regeneration process is completed may be regarded as the PM deposition restart time.

By continuously monitoring the output value of the PM sensor, it may be possible to continuously grasp the behavior of the output value of the PM sensor. Then, the PM trapping function of the SCRF may be diagnosed, based on the behavior of the output value of the PM sensor when the NOx converting function of the SCRF is in a normal status. More specifically, if the output value of the PM sensor is reduced when it is determined that the NOx converting function of the SCRF is in a normal status, the ECU may determine that there is an abnormality in the PM trapping function of the SCRF.

The PM flowing out from the SCRF may be continuously trapped between the electrodes of the PM sensor. Therefore, the output value of the PM sensor may continuously increase as the PM deposition amount continuously increases. On the other hand, if aqueous urea flows out from the SCRF, and the aqueous urea is attached to between the electrodes of the PM sensor, a part of the PM deposited between the electrodes may be peeled off by the aqueous urea. In this case, the amount of PM deposited between the electrodes may be reduced, and the output value of the PM sensor may be reduced. Accordingly, when the output value of the PM sensor, which has continuously increased, is reduced after the PM deposition restart time, this behavior of the output value of the PM sensor may be highly likely to indicate that aqueous urea is attached to between the electrodes of the PM sensor. Then, if the NOx converting function of the SCRF is in a normal status at this time, it can be determined that the outflow of aqueous urea may be caused by deterioration of the PM trapping function due to a failure, such as breakage or erosion, in the SCRF. Therefore, if the output value of the PM sensor exhibits the above-described behavior when it is determined that the NOx converting function of the SCRF is in a normal status, it may be determined that there is an abnormality in the PM trapping function of the SCRF.

As described above, the PM trapping function of the SCRF may be diagnosed using the output value of the PM sensor provided in the exhaust passage downstream of the SCRF. Also, the PM trapping function of the SCRF may be diagnosed, without limiting supply of aqueous urea to the SCRF. Accordingly, the NOx conversion rate in the SCRF may be less likely or unlikely to be reduced due to limitation on injection of aqueous urea from the aqueous urea addition device (for example, reduction of the injection amount or stopping of injection).

In the function diagnostic system according to the above aspect of the disclosure, when the output value of the PM sensor, which has been continuously monitored, is not reduced when the electronic control unit determines that the NOx converting function of the filter is in the normal status, the ECU may be configured to diagnose the PM trapping function of the filter, based on the output value of the PM sensor at a time when a predetermined determination period elapses from the PM deposition restart time. With this arrangement, if there is no reduction of the output value of the PM sensor due to the influence of aqueous urea until the predetermined determination period elapses from the PM deposition restart time, the PM trapping function of the SCRF may be diagnosed, based on the output value of the PM sensor obtained at the time when the determination period elapses from the PM deposition restart time.

Suppose the function diagnostic system diagnoses the PM trapping function only based on the output value of the PM sensor obtained at the time when the determination period elapses from the PM deposition restart time. In this case, if the PM trapping function is diagnosed only based on the output value of the PM sensor obtained at the time when the determination period elapses from the PM deposition restart time, it may be erroneously determined that the PM trapping function of the SCRF is in a normal status, even though there is actually an abnormality in the PM trapping function of the SCRF, when the output value of the PM sensor is reduced due to attachment of aqueous urea to between the electrodes of the PM sensor during the predetermined determination period. Also, in this case, it may be considered to inhibit a diagnosis of the PM trapping function of the SCRF from being conducted when the output value of the PM sensor is reduced during the predetermined determination period. However, in this case, the diagnosis of the PM trapping function of the SCRF may be conducted only when there was no reduction of the output value of the PM sensor during the predetermined determination period. This may make it difficult to ensure a sufficiently high frequency with which the diagnosis of the filter function is conducted. These problems may be solved by combining two types of diagnoses of the PM trapping function, as in the arrangement of the disclosure as described above.

In the function diagnostic system according to the above aspect of the disclosure, when the output value of the PM sensor, which has been continuously monitored, is reduced when the electronic control unit determines that the NOx converting function of the filter is in the normal status, the ECU may be configured to limit injection of aqueous urea from the aqueous urea addition device after the PM deposition restart time, and diagnose the PM trapping function of the filter based on the output value of the PM sensor at a time when a predetermined determination period elapses from the PM deposition restart time. With this arrangement, the PM trapping function of the SCRF may be diagnosed in a condition where an influence of aqueous urea on the output value of the PM sensor is reduced. Therefore, the PM trapping function of the SCRF may be diagnosed with higher accuracy. It may be determined, as a diagnostic result, that there is an abnormality in the PM trapping function of the SCRF if the output value of the PM sensor, which has been continuously monitored, is reduced when it is determined that the NOx converting function of the SCRF is in a normal status, and injection of aqueous urea from the aqueous urea addition device is limited only when this diagnostic result is obtained. Thus, the frequency of execution of limitation on injection of aqueous urea may be reduced, as compared with the case where injection of aqueous urea from the aqueous urea addition device is limited each time the diagnosis of the PM trapping function of the SCRF is conducted. Accordingly, the NOx conversion rate in the SCRF may be less likely or unlikely to be reduced due to the limitation on injection of aqueous urea.

It may be found that, in the exhaust system of the internal combustion engine, a part of the PM discharged from the engine may be once attached to a wall of the exhaust passage, or various structures (which will be called "exhaust-system structures"), such as a downstream end face of the SCRF, catalyst, and a reducing agent addition device (including the aqueous area addition device), provided in the exhaust passage, before it reaches the PM sensor. It may be also found that the attached PM may be peeled off and reach the PM sensor, where the peeled PM is trapped between the electrodes of the PM sensor. In the following, the PM peeled off from the wall of the exhaust passage or the exhaust-system structures after being once attached to the wall or exhaust-system structures will be called "peeled PM". When normal PM contained in exhaust gas discharged from the engine needs to be distinguished from the "peeled PM", the normal PM will be called "normal PM".

If the peeled PM is generated and trapped between the electrodes of the PM sensor, during a period from the voltage application time to the time when the predetermined determination period elapses, the output value of the PM sensor may behave or change in a different manner from that in the case where normal PM is trapped between the electrodes. More specifically, if the peeled PM is trapped between the electrodes of the PM sensor, the output value of the PM sensor may increase accordingly. It is, however, to be noted that the peeled PM trapped between the electrodes of the PM sensor may be more likely to be removed from between the electrodes, as compared with the normal PM. If the peeled PM once trapped between the electrodes of the PM sensor is removed from between the electrodes, the output value of the PM sensor may be reduced. Namely, it is found that, when the peeled PM is generated and trapped between the electrodes of the PM sensor, during the period from the voltage application time to the time of expiration of the determination period, the output value of the PM sensor may be reduced even when the PM trapping function of the SCRF is in a normal status.

In the function diagnostic system according to the above aspect of the disclosure, the ECU may be configured to determine whether a predetermined peeled PM generation condition is satisfied. The peeled PM generation condition may be a condition under which a phenomenon that the PM once attached to a wall of the exhaust passage or an exhaust-system structure is peeled off from the wall of the exhaust passage or the exhaust-system structure can occur. The ECU may be configured to diagnose the PM trapping function of the filter, based on the output value of the PM sensor which has been continuously monitored, when the electronic control unit determines that the NOx converting function of the filter is in the normal status, and the electronic control unit may determine that the peeled PM generation condition is not satisfied. With this arrangement, it is less likely or unlikely to be erroneously determined that there is an abnormality in the PM trapping function of the SCRF, due to the influence of the peeled PM, even though the PM trapping function of the SCRF is actually in a normal status.

As the amount of the PM deposited on the wall of the exhaust passage or the exhaust-system structure increases, the peeled PM may be more likely to be generated. In the function diagnostic system as described above, the ECU may be configured to control the internal combustion engine such that a filter regeneration process for oxidizing and removing the PM deposited in the filter is executed. The ECU may be configured to determine whether the peeled PM generation condition is satisfied, based on an integrated value of an amount of PM discharged from the internal combustion engine after completion of the filter regeneration process. If the filter regeneration process is carried out, not only the PM deposited in the SCRF, but also the PM attached to the wall of the exhaust passage or the exhaust-system structure, may be highly likely to be oxidized and removed. Then, once the filter regeneration process is completed, the PM may start being attached again to the wall of the exhaust passage or the exhaust-system structure, as the PM is discharged from the internal combustion engine. Therefore, there may be a correlation between the amount of PM deposited on the wall of the exhaust passage or the exhaust-system structure, and the integrated value of the PM discharge amount. Accordingly, it may be determined whether the peeled PM generation condition is satisfied, based on the integrated value of the PM discharge amount. More specifically, if the integrated value of the PM discharge amount is equal to or larger than a predetermined criterial integrated value, it may be determined that the peeled PM generation condition is satisfied.

As the flow rate of exhaust gas flowing in the exhaust passage is larger, the peeled PM is more likely to be generated. In the function diagnostic system as described above, the ECU may be configured to determine whether the peeled PM generation condition is satisfied, based on the flow rate of exhaust gas flowing in the exhaust passage, in addition to the integrated value of the amount of PM discharged from the internal combustion engine after completion of the filter regeneration process. More specifically, the criterial integrated value as a threshold value for determining whether the peeled PM generation condition is satisfied, based on the integrated value of the PM discharge amount, may be set to a smaller value as the flow rate of exhaust gas is larger.

The function diagnostic system according to the above aspect of the disclosure may be able to diagnose the PM trapping function of the SCRF, using the output value of the PM sensor provided in the exhaust passage downstream of the SCRF.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 7A is a view showing images of a portion of the PM sensor between the electrodes when the output value of the PM sensor exhibits the behavior as indicated in a portion of line L3 of FIG. 6 surrounded by broken line a;

DETAILED DESCRIPTION OF EMBODIMENTS

Disclosed embodiments will be described with reference to the drawings. The dimensions, materials, shapes, relative arrangements, etc. of constituent components described in the embodiments are not supposed to limit the technical scope of the disclosure to those described below, unless otherwise specified.

Figure 1:
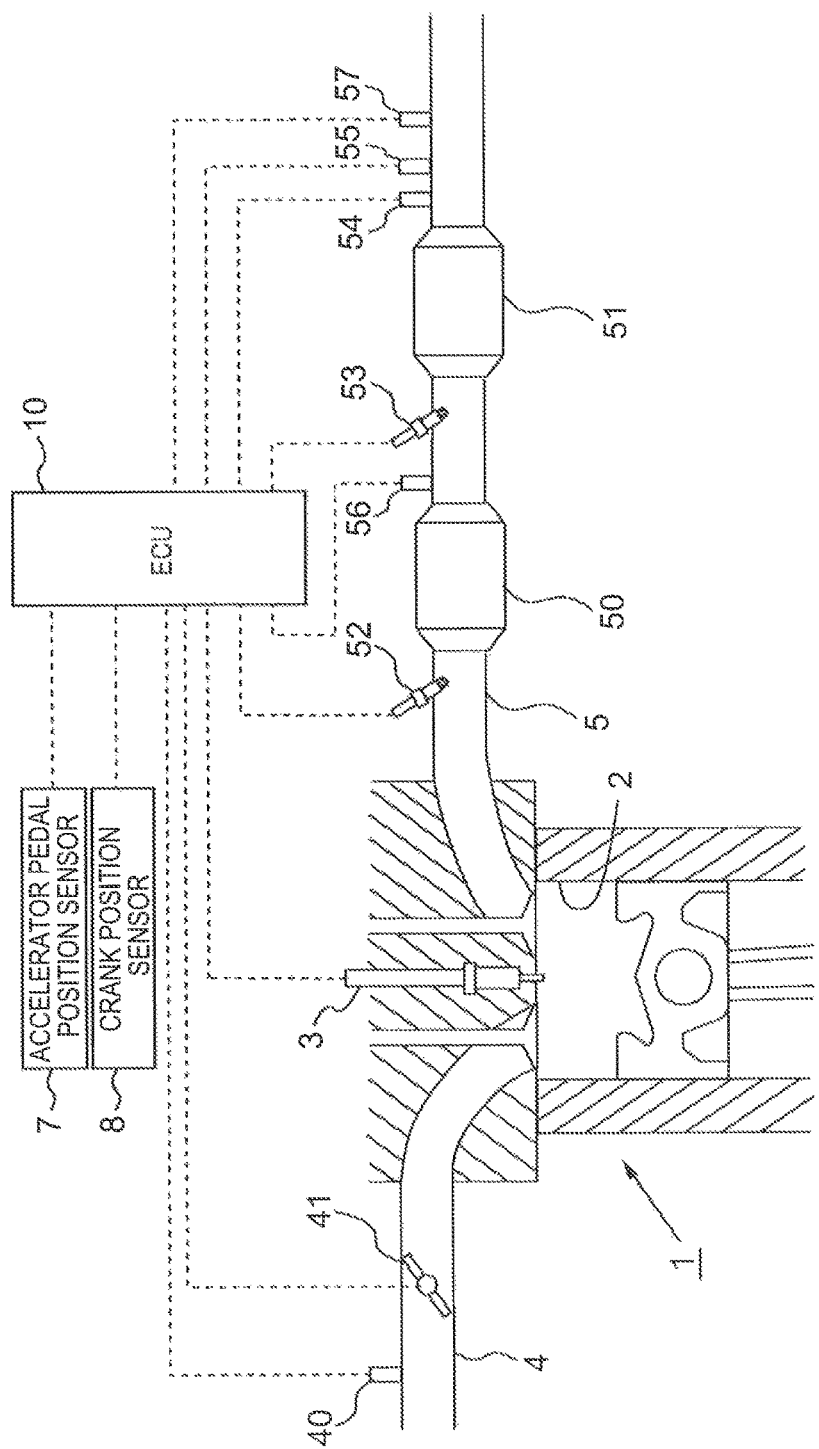
FIG. 1 is a view schematically showing the configuration of an internal combustion engine and its intake and exhaust systems according to some embodiments.

FIG. 1 schematically shows the configuration of an internal combustion and its intake and exhaust systems according to some embodiments. The engine 1 shown in FIG. 1 is a compression ignition type internal combustion engine (diesel engine) using light oil as fuel. The engine 1 may be a spark ignition type internal combustion engine using gasoline, or the like, as fuel.

The internal combustion engine 1 includes a fuel injection valve 3 that injects the fuel into a cylinder 2. In the case where the engine 1 is a spark ignition type internal combustion engine, the fuel injection valve 3 may be configured to inject the fuel into an intake port.

The internal combustion engine 1 is connected to an intake passage 4. An air flow meter 40 and an intake throttle valve 41 are provided in the intake passage 4. The air flow meter 40 outputs an electric signal corresponding to the amount (mass) of intake air (air) flowing in the intake passage 4. The intake throttle valve 41 is located downstream of the air flow meter 40 in the intake passage 4. The intake throttle valve 41 is operable to change the cross-sectional area of the intake passage 4 so as to adjust the intake air amount of the engine 1.

The internal combustion engine 1 is connected to an exhaust passage 5. An oxidation catalyst 50, SCRF 51, fuel addition valve 52, and an aqueous urea addition valve 53, which constitute an emission control system, are provided in the exhaust passage 5. The SCRF 51 is a wall-flow type filter formed from a porous substrate, and a SCR catalyst is supported by the substrate of the filter. The SCRF 51 thus constructed has a PM trapping function of trapping PM (particulate matter) in exhaust gas, and a NOx converting function of reducing NOx in exhaust gas, using ammonia as a reducing agent. The oxidation catalyst 50 is provided in the exhaust passage 5 upstream of the SCRF 51. The fuel addition valve 52 is provided in the exhaust passage 5 further upstream of the oxidation catalyst 50. The fuel addition valve 52 injects fuel into the exhaust gas flowing in the exhaust passage 5. The aqueous urea addition valve 53 is provided in the exhaust passage 5 downstream of the oxidation catalyst 50 and upstream of the SCRF 51. The aqueous urea addition valve 53 injects aqueous urea into the exhaust gas flowing in the exhaust passage 5. When aqueous urea is injected from the aqueous urea addition valve 53 into the exhaust gas, the aqueous urea is supplied to the SCRF 51. In the SCRF 51, the aqueous urea thus supplied is hydrolyzed to generate ammonia, which is adsorbed on the SCR catalyst. Then, NOx in the exhaust gas is reduced, using ammonia adsorbed on the SCR catalyst, as a reducing agent. Namely, the SCRF 51 performs the NOx converting function when aqueous urea is supplied from the aqueous urea addition valve 53 to the SCRF 51.

An upstream NOx sensor 56 is provided in the exhaust passage 5 downstream of the oxidation catalyst 50 and upstream of the aqueous urea addition valve 53. A downstream NOx sensor 57 is provided in the exhaust passage 5 downstream of the SCRF 51. Each of the upstream NOx sensor 56 and the downstream NOx sensor 57 outputs an electric signal corresponding to the NOx concentration of the exhaust gas. Also, a temperature sensor 54 and a PM sensor 55 are provided in the exhaust passage 5 downstream of the SCRF 51. The temperature sensor 54 outputs an electric signal corresponding to the temperature of the exhaust gas. The PM sensor 55 outputs an electric signal correlated to the amount of PM flowing out from the filter 51.

Figure 2:
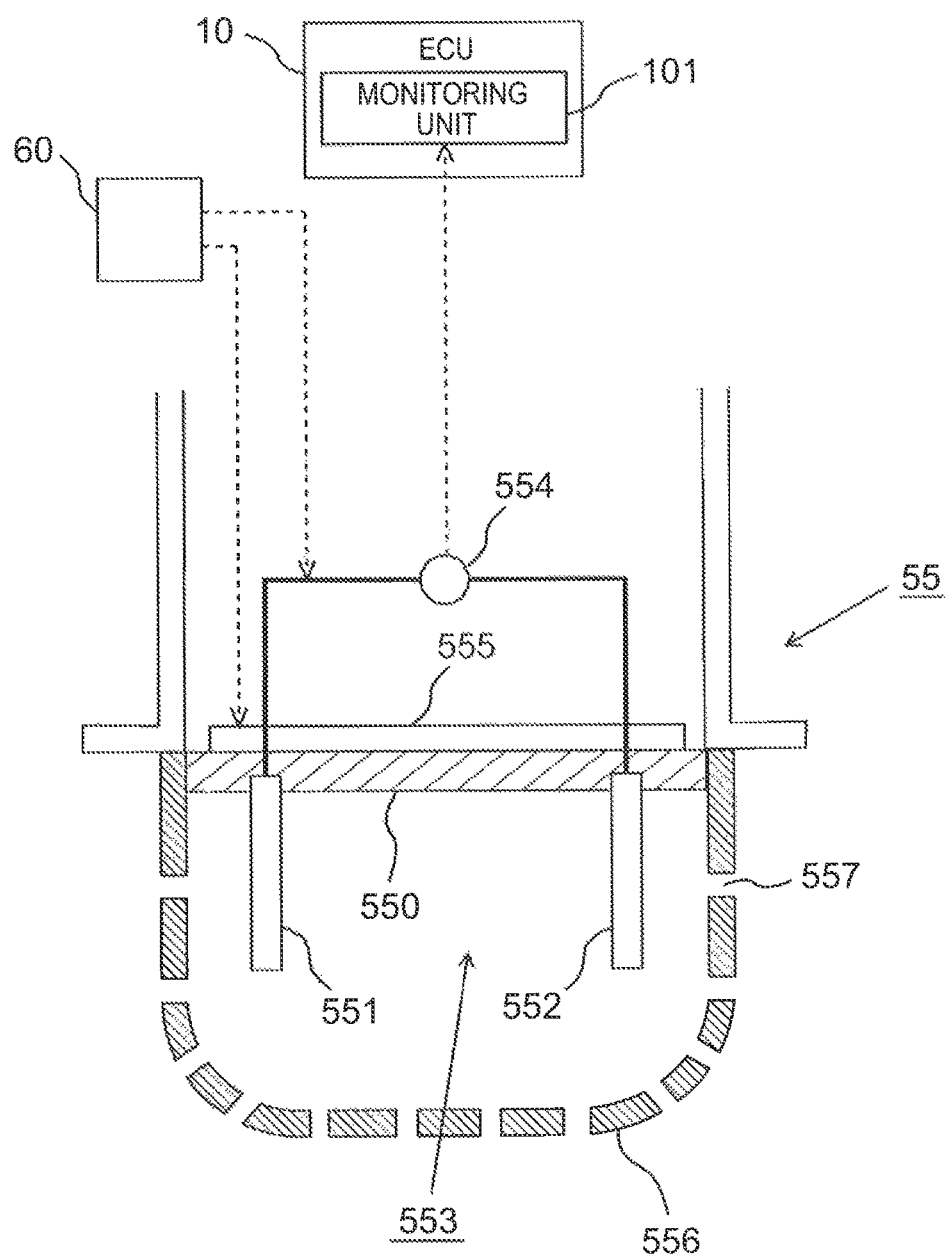
FIG. 2 is a view schematically showing the configuration of a PM sensor according to the some embodiments.

The configuration of the PM sensor 55 will be described with reference to FIG. 2. FIG. 2 schematically shows the configuration of the PM sensor 55. The PM sensor 55 is an electrode-type PM sensor. While a pair of electrodes are illustrated in FIG. 2, two or more pairs of electrodes may be provided.

The PM sensor 55 includes a sensor element 553, ammeter 554, heater 555, and a cover 556. The sensor element 553 consists of a pair of electrodes 551, 552 disposed on a surface of a plate-like insulator 550 such that the electrodes 551, 552 are spaced apart from each other. The ammeter 554 measures current flowing between the electrodes 551, 552. The heater 555 is an electrothermal heater disposed on a rear surface of the insulator 550. The cover 556 covers the sensor element 553. A plurality of through-holes 557 are formed in the cover 556. Electric power is supplied from a power supply 60 provided in the outside, to the electrodes 551, 552 and heater 555 of the PM sensor 55. Then, an output value corresponding to a current value measured by the ammeter 554 is generated from the PM sensor 55.

If the PM sensor 55 constructed as described above is installed in the exhaust passage 5, a part of exhaust gas flowing in the exhaust passage 5 passes through the through-holes 557, and flows into the inside of the cover 556. Then, the PM contained in the exhaust gas flowing into the cover 556 is trapped between the electrodes 551, 552. If a voltage is applied to the electrodes 551, 552 at this time, trapping of the PM between the electrodes 551, 552 is promoted.

Figure 3:
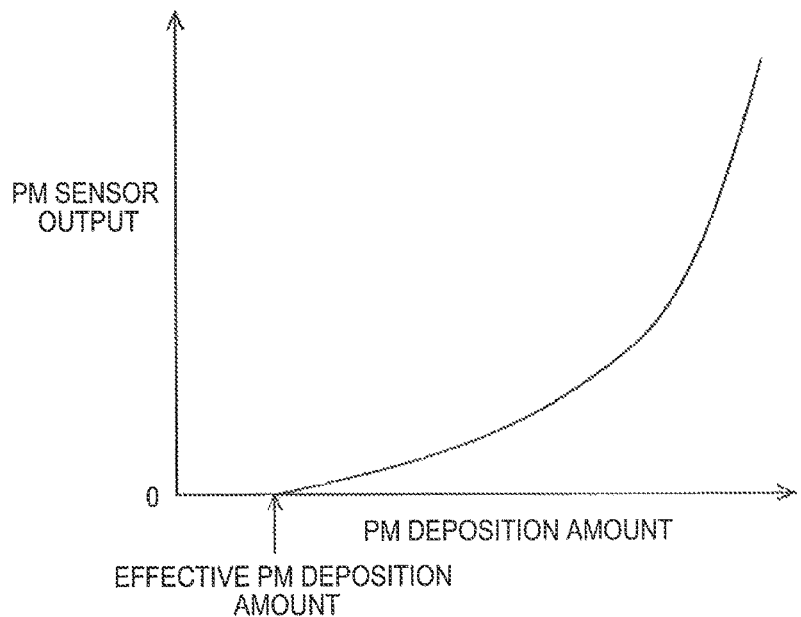
FIG. 3 is a view showing the relationship between the amount of PM deposited between electrodes of the PM sensor and the output value of the PM sensor according to some embodiments.

The relationship between the amount of PM deposited between the electrodes 551, 552, and the output value of the PM sensor 55. In FIG. 3, the horizontal axis indicates the amount of PM deposited between the electrodes 551, 552, and the vertical axis indicates the output value of the PM sensor 55. As the PM is trapped between the electrodes 551, 552, the amount of PM deposited between the electrodes 551, 552 gradually increases. At this time, if voltage is applied across the electrodes 551, 552, and a given amount of PM is deposited between the electrodes 551, 552, until the PM thus deposited extends from one electrode 551 to the other electrode 551, the electrodes 551, 552 are electrically conducted by the PM since the PM has electrical conductivity. However, if the amount of PM deposited between the electrodes 551, 552 is smaller than the given amount, the electrodes 551, 552 are in a non-conduction state. The PM deposition amount that brings the electrodes 551, 552 into a conduction state will be called "effective PM deposition amount".

As shown in FIG. 3, the electrodes 551, 552 are in the non-conduction state until the amount of PM deposited between the electrodes 551, 552 reaches the effective PM deposition amount; therefore, the output value of the PM sensor 55 is equal to zero. Then, if the amount of PM deposited between the electrodes 551, 552 becomes equal to or larger than the effective PM deposition amount, electric resistance between the electrodes 551, 552 is reduced as the amount of PM deposited between the electrodes 551, 552 increases. As a result, current that flows between the electrodes 551, 552 increases. Accordingly, the output value of the PM sensor increases in accordance with increase of the amount of PM deposited between the electrodes 551, 552. In the following description, the time at which the output value of the PM sensor 55 starts increasing from zero will be called "output start time". As the amount of PM deposited between the electrodes 551, 552 increases, the amount of reduction of electric resistance between the electrodes 551, 552 relative to the amount of increase of the PM deposition amount increases; as a result, the amount of increase of the current flowing between the electrodes 551, 552 increases. Therefore, as the amount of PM deposited between the electrodes 551, 552 increases, the amount of increase of the output value of the PM sensor 55 relative to the amount of increase of the PM deposition amount increases.

Referring back to FIG. 1, the internal combustion engine 1 is equipped with an electronic control unit (ECU). The ECU 10 is a controller that controls operating conditions, etc. of the engine 1. The ECU 10 may be electronically programmed to perform disclosed functions. Various sensors, including an accelerator pedal position sensor 7 and a crank position sensor 8, in addition to the above-mentioned air flow meter 40, upstream NOx sensor 56, downstream NOx sensor 57, temperature sensor 54, and the PM sensor 55, are electrically connected to the ECU 10. The accelerator pedal position sensor 7 outputs an electric signal correlated to the amount of operation (acceleration stroke) of an accelerator pedal (not shown). The crank position sensor 8 outputs an electric signal correlated to the rotational position of an engine output shaft (crankshaft) of the engine 1. The ECU 10 receives the output signals of these sensors. The output signal of the PM sensor 55 is transmitted to a monitoring unit 101 of the ECU 10. Namely, in this embodiment, the monitoring unit 101 of the ECU 10 is able to continuously monitor the output value of the PM sensor 55. When the PM sensor 55 is provided with a sensor control unit (sub ECU) for controlling the PM sensor 55, the sub ECU may include a monitoring unit that continuously monitors the output value of the PM sensor 55.

Also, various devices, including the above-mentioned fuel injection valve 3, intake throttle valve 41, fuel addition valve 52, and aqueous urea addition valve 53, are electrically connected to the ECU 10. The ECU 10 controls these various devices, based on the output signals of the sensors as described above. For example, the ECU 10 controls the amount of aqueous urea injected from the aqueous urea addition valve 53, so as to keep the amount of ammonia adsorbed in the SCRF 51 (i.e., the amount of ammonia adsorbed on the SCR catalyst) equal to a target adsorption amount. The target adsorption amount is a value that is determined in advance by experiment, or the like, as a value that can ensure a desired NOx conversion rate (the ratio of the amount of NOx reduced in the SCRF 51, to the amount of NOx flowing into the SCRF 51) in the SCRF 51, while keeping the amount of ammonia flowing from the SCRF 51 within a permissible range.

When an estimated value of the PM deposition amount in the SCRF 51 reaches a predetermined threshold value, the ECU 10 performs a filter regeneration process by controlling the amount of fuel injected from the fuel addition valve 52 of the internal combustion engine 1. In the filter regeneration process, the temperature of the SCRF 51 is raised by oxidation heat produced when the fuel injected from the fuel addition valve 52 is oxidized in the oxidation catalyst 50. At this time, the ECU 10 controls the amount of fuel injected from the fuel addition valve 52, so that the temperature of the SCRF 51 estimated based on the output value of the temperature sensor 54 becomes equal to a target temperature. The target temperature is a value that is determined in advance by experiment, or the like, as a temperature at which the PM can be oxidized. As a result, the PM deposited in the SCRF 51 is burned and removed. The amount of PM deposited in the SCRF 51 may be estimated based on an integrated value of the amount of fuel injected from the fuel injection valve 3, from the time when the last filter regeneration process is completed, and the temperature history of the SCRF 51, for example. Also, the filter regeneration process may be executed each time the integrated value of the amount of fuel injected from the fuel injection valve 3 reaches a predetermined regeneration execution threshold value.

Figure 4:
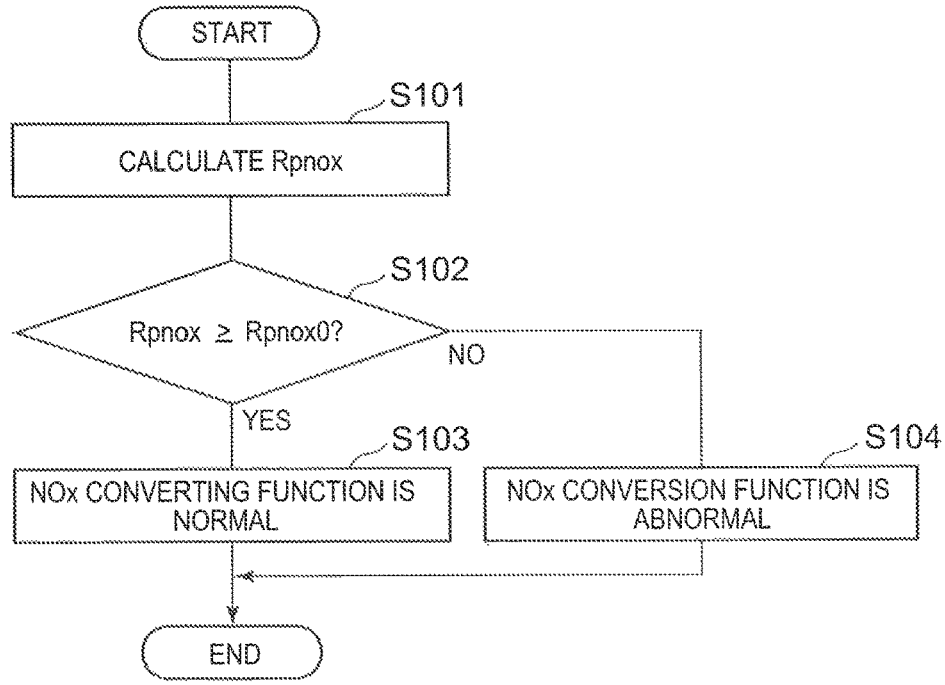
FIG. 4 is a flowchart illustrating the flow of control for diagnosing the NOx converting function of a SCRF according to some embodiments.

If the SCR catalyst supported on the SCRF 51 deteriorates, the NOx converting function of the SCRF 51 declines, resulting in increase of the amount of NOx released to the atmosphere. Thus, in this embodiment, the NOx converting function of the SCRF 51 is diagnosed. In the following, a method of diagnosing the NOx converting function of the SCRF according to this embodiment will be described with reference to FIG. 4. FIG. 4 is a flowchart illustrating the flow of control for diagnosing the NOx converting function of the SCRF according to this embodiment. The control flow is executed by the ECU 10 when a certain condition for diagnosing the NOx converting function is satisfied. The condition for diagnosing the NOx converting function is a condition under which a diagnosis of the NOx converting function of the SCRF 51 is carried out. The condition for diagnosing the NOx converting function is set so that the diagnosis of the NOx converting function of the SCRF 51 can be carried out with necessary and sufficient frequency. As one example of the condition for diagnosing the NOx converting function, a predetermined period of diagnosis of the NOx converting function has elapsed from the last execution of the flow of FIG. 4, AND the temperature of the SCRF 51 is within an activation temperature range of the SCR catalyst supported on the SCRF 51.

In the flow of FIG. 4, initially in step S101, the NOx conversion rate Rpnox in the SCRF 51 is calculated based on the output value of the upstream NOx sensor 56 and the output value of the downstream NOx sensor 57. Then, in step S102, it is determined whether the NOx conversion rate Rpnox in the SCRF 51, which is calculated in step S101, is equal to or higher than a predetermined criterial conversion rate Rpnox0. The criterial conversion rate Rpnox0 is a threshold value based on which it can be determined that the NOx converting function of the SCRF 51 is in a normal status. The criterial conversion rate Rpnox0 may be a fixed value that is determined in advance by experiment, or the like. Even if the NOx converting function of the SCRF 51 is in a normal status, the NOx conversion rate in the SCRF 51 changes according to the amount of ammonia adsorbed in the SCRF 51. Thus, the amount of ammonia adsorbed in the SCRF 51 is estimated on the assumption that the NOx converting function of the SCRF 51 is in a normal status, and the criterial conversion rate Rpnox0 may be determined based on the estimated value. In this case, any of known methods for estimating the amount of ammonia adsorbed on the SCR catalyst may be employed, as a method of estimating the amount of ammonia adsorbed in the SCRF 51 on the assumption that the NOx converting function of the SCRF 51 is in a normal status.

When an affirmative decision (YES) is made in step S102, namely, when the NOx conversion rate Rpnox in the SCRF 51 is equal to or higher than the predetermined criterial conversion rate Rpnox0, it is then determined in step S103 that the NOx converting function of the SCRF 51 is in a normal status. On the other hand, when a negative decision (NO) is made in step S102, namely, when the NOx conversion rate Rpnox in the SCRF 51 is lower than the predetermined criterial conversion rate Rpnox0, it is then determined in step S104 that there is an abnormality in the NOx converting function of the SCRF 51 (namely, the SCR catalyst supported on the SCRF 51 is deteriorated). If it is determined in step S104 that there is an abnormality in the NOx converting function of the SCRF 51, this result of diagnosis is stored in the ECU 10.

In the SCRF 51, a failure, such as breakage or erosion, may occur due to the elevated temperature, etc. caused by execution of the filter regeneration process. If such a failure occurs, the PM trapping function of the SCRF 51 declines, resulting in increase of the amount of PM released to the atmosphere. Thus, in this embodiment, the PM trapping function of the SCRF 51 is diagnosed, using the output value of the PM sensor 55. In the following, a method of diagnosing the PM trapping function of the SCRF according to this embodiment will be described.

In the method of diagnosing the PM trapping function of the SCRF according to this embodiment, a sensor regeneration process for removing the PM deposited between the electrodes 551, 552 of the PM sensor 55 is initially carried out. More specifically, electric power is supplied from the power supply 60 to the heater 555, so that the sensor element 553 is heated by the heater 555. As a result, the PM deposited between the electrodes 551, 552 is oxidized and removed. In the sensor regeneration process, the amount of electric power supplied to the heater 555 is adjusted, so that the temperature of the sensor element 553 is controlled to a temperature at which the PM can be oxidized.

If the PM deposited between the electrodes 551, 552 is removed through the sensor regeneration process, a voltage starts being applied from the power supply 60 to the electrodes 551, 552. In the following, the time at which a voltage starts being applied to the electrodes 551, 552 will be called "voltage application time". After completion of the sensor regeneration process, the temperature of the electrodes 551, 552 remains high for a while. Therefore, a cooling period for cooling the electrodes 551, 552 may be provided between completion of the sensor regeneration process and the voltage application time. Also, if a voltage is applied to the electrodes 551, 552, trapping of PM between the electrodes 551, 552 is promoted, as described above. Therefore, in this embodiment, the voltage application time corresponds to the PM deposition restart time according to some embodiments. Also, in this embodiment, a voltage may start being applied to the electrodes 551, 552 during execution of the sensor regeneration process. In this case, the time at which the sensor regeneration process is completed (namely, the time at which supply of electric power to the heater 555 is stopped) may be regarded as the PM deposition restart time according to some embodiments. Also, in this case, a point of time at which a given period after which it can be determined that the temperature of the electrodes 551, 552 of the PM sensor 55 has been lowered to such a level that the trapped PM is not oxidized has elapsed from the time of completion of the sensor regeneration process may be regarded as the PM deposition restart time according to some embodiments.

Figure 5:
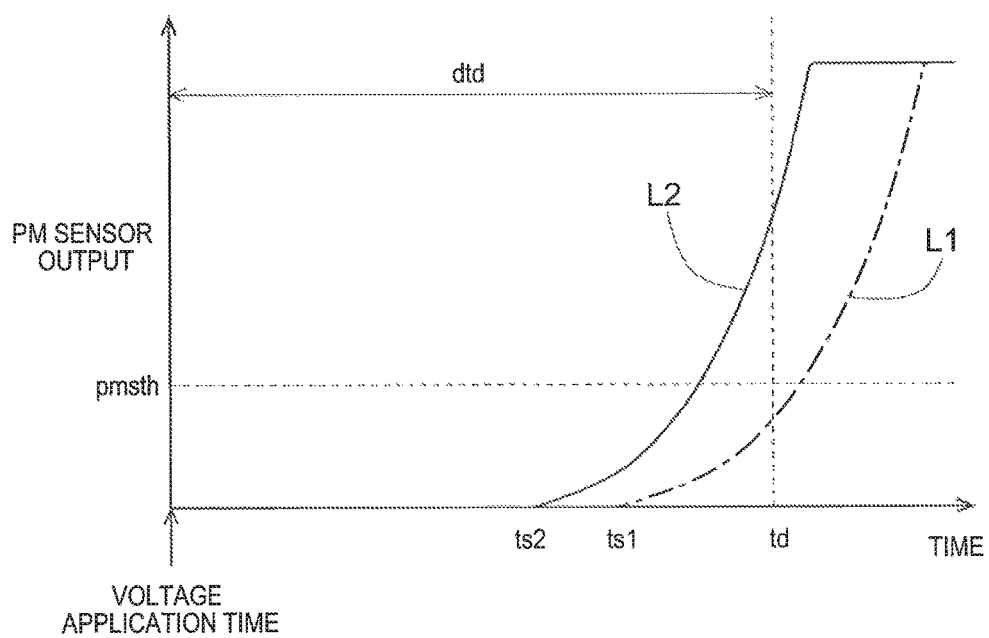
FIG. 5 is a first view showing changes in the output value of the PM sensor with time after a voltage application time according to some embodiments.

The behavior of the output value of the PM sensor 55 after a voltage starts being applied to the electrodes 551, 552 will be described with reference to FIG. 5. FIG. 5 shows changes in the output value of the PM sensor 55 with time after the voltage application time. In FIG. 5, the horizontal axis indicates the elapsed time from the voltage application time, and the vertical axis indicates the output value of the PM sensor 55. In FIG. 5, line L1 and line L2 indicate the output values of the PM sensor 55 when the PM trapping function of the SCRF 51 is in different statuses while the internal combustion engine 1 is in the same operating conditions. Namely, line L1 shows changes in the output value of the PM sensor 55 with time when the PM trapping function of the SCRF 51 is in a normal status, and line L2 shows changes in the output value of the PM sensor 55 with time when there is an abnormality in the PM trapping function of the SCRF 51. In FIG. 5, ts1 indicates the output start time when the PM trapping function of the SCRF 51 is in a normal status, and ts2 indicates the output start time when there is an abnormality in the PM trapping function of the SCRF 51.

If the PM trapping function of the SCRF 51 declines, the amount of PM flowing out from the SCRF 51 per unit time (PM discharge amount) increases. As the PM discharge amount increases, the amount of PM that reaches the PM sensor 55 and is trapped between the electrodes 551, 552 increases. Namely, the rate of increase of the amount of PM deposited between the electrodes 551, 552 increases. As a result, if the PM trapping function of the SCRF 51 is brought into an abnormal status, the amount of PM deposited between the electrodes 551, 552 reaches the effective PM deposition amount at an earlier point in time, as compared with the time when the PM trapping function of the SCRF 51 is in a normal status. Accordingly, as shown in FIG. 5, when the PM trapping function of the SCRF 51 is in an abnormal status, the period from the voltage application time to the output start time is shortened (ts2<ts1), as compared with the case where the PM trapping function of the SCRF 51 is in a normal status. Also, if the PM trapping function of the SCRF 51 is brought into an abnormal status, the rate of increase of the amount of PM deposited between the electrodes 551, 552 after the output start time becomes larger, as compared with the time when the PM trapping function of the SCRF 51 is in a normal status. Accordingly, as shown in FIG. 5, when the PM trapping function of the SCRF 51 is in an abnormal status, the rate of increase of the output value of the PM sensor 55 per unit time after the output start time becomes larger, as compared with the case where the PM trapping function of the SCRF 51 is in a normal status.

The differences as described above appear in the behavior of the output value of the PM sensor 55 between the time when the PM trapping function of the SCRF 51 is in a normal status, and the time when there is an abnormality in the PM trapping function of the SCRF 51. As a result, when there is an abnormality in the PM trapping function of the SCRF 51, the output value of the PM sensor 55 after a certain period of time elapses from the voltage application time is larger than that in the case where the PM trapping function of the SCRF 51 is in a normal status. Thus, in this embodiment, the PM trapping function of the SCRF 51 is diagnosed, based on the output value of the PM sensor 55 at a determination time td after a predetermined determination period dtd has elapsed from the voltage application time. More specifically, when the output value of the PM sensor 55 at the determination time td is equal to or larger than a predetermined abnormality determination value pmsth, it is determined that there is an abnormality in the PM trapping function of the SCRF 51.

In this connection, the determination period dtd is set as a period from the voltage application time, to the time when a reference value of the amount of PM deposited between the electrodes 551, 552 of the PM sensor 55 (which will be called "reference PM deposition amount") reaches a predetermined criterial PM deposition amount. The reference PM deposition amount is a value estimated on the assumption that the PM trapping function of the SCRF 51 is in a reference failed status. The reference failed status means a failed status having the smallest degree of fault, out of failed statuses in which it should be determined that there is an abnormality in the PM trapping function of the SCRF 51 in the diagnosis of the PM trapping function of the SCRF. Namely, even in a condition where the PM trapping function of the SCRF 51 declines to some extent, it is determined, in the diagnosis of the PM trapping function of the SCRF, that the PM trapping function of the SCRF 51 is in a normal status if this condition is better than the reference failed status (namely, if the degree of breakage or erosion is small). The abnormality determination value pmsth is set to the output value of the PM sensor 55 when the amount of PM deposited between the electrodes 551, 552 of the PM sensor 55 is equal to the criterial PM deposition amount.

The reference PM deposition amount is calculated by estimating the amount of PM trapped between the electrodes 551, 552 of the PM sensor 55 (which will be simply called "trapped PM amount") when it is assumed that the PM trapping function of the SCRF 51 is in the reference failed status, and integrating the estimated value of the trapped PM amount. Even in the case where the PM trapping function of the SCRF 51 is in the same status, the amount of PM flowing out from the SCRF 51 varies, according to the operating conditions (such as the amount of fuel injected from the fuel injection valve 3, the flow rate of exhaust gas, etc.) of the engine 1, and the PM deposition amount in the SCRF 51. Also, the ratio of the PM trapped between the electrodes 551, 552 of the PM sensor 55 to the amount of PM contained in exhaust gas (which will be called "PM trapping ratio) varies according to the flow rate of the exhaust gas. Therefore, when the trapped PM amount is estimated assuming that the PM trapping function of the SCRF 51 is in the reference failed status, the operating conditions of the engine 1 and the PM deposition amount in the SCRF 51 are also taken into consideration. Any known method may be used as a specific method of calculating the reference PM deposition amount.

As described above, in this embodiment, aqueous urea injected from the aqueous urea addition valve 53 is supplied to the SCRF 51. It is found that, even if there is an abnormality in the PM trapping function of the SCRF 51, the NOx converting function of the SCRF 51 can be in a normal status. However, if there is an abnormality in the PM trapping function of the SCRF 51, the aqueous urea supplied to the SCRF 51 may flow out from the SCRF 51 even if the NOx converting function of the SCRF 51 is in a normal status. This may be because aqueous urea may slip through a broken (or melt) portion of the SCRF 51. If aqueous urea flows out from the SCRF 51, the aqueous urea may reach the PM sensor 55, and may be attached to between the electrodes 551, 552 of the PM sensor 55. At this time, if a voltage is applied to the electrodes 551, 552 of the PM sensor 55, and the PM is deposited between the electrodes 551, 552, the output value of the PM sensor 55 is influenced by the aqueous urea.

Figure 6:
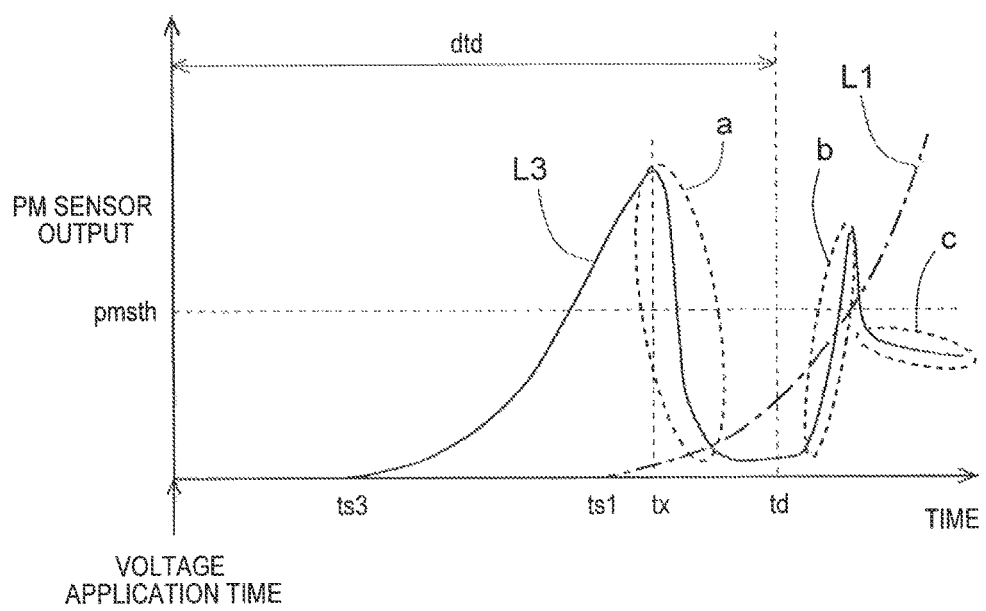
FIG. 6 is a second view showing changes in the output value of the PM sensor with time after the voltage application time according to some embodiments.

The influence of aqueous urea on the output value of the PM sensor 55 when aqueous urea is injected from the aqueous urea addition valve 53 after the voltage application time and the aqueous urea flowing out from the SCRF 51 is attached to between the electrodes 551, 552 of the PM sensor 55 will be described with reference to FIG. 6 and FIG. 7. Like FIG. 5, FIG. 6 shows changes in the output value of the PM sensor 55 with time after the voltage application time. In FIG. 6, the horizontal axis indicates the elapsed time from the voltage application time, and the vertical axis indicates the output value of the PM sensor 55. Also, line L1 in FIG. 6, which is similar to line L1 in FIG. 5, indicates changes in the output value of the PM sensor 55 with time when the PM trapping function of the SCRF 51 is in a normal status. In FIG. 6, line L3 indicates the output value of the PM sensor 55 when there is an abnormality in the PM trapping function of the SCRF 51, and aqueous urea flowing out from the SCRF 51 is attached to between the electrodes 551, 552 of the PM sensor 55.

Figure 7A:
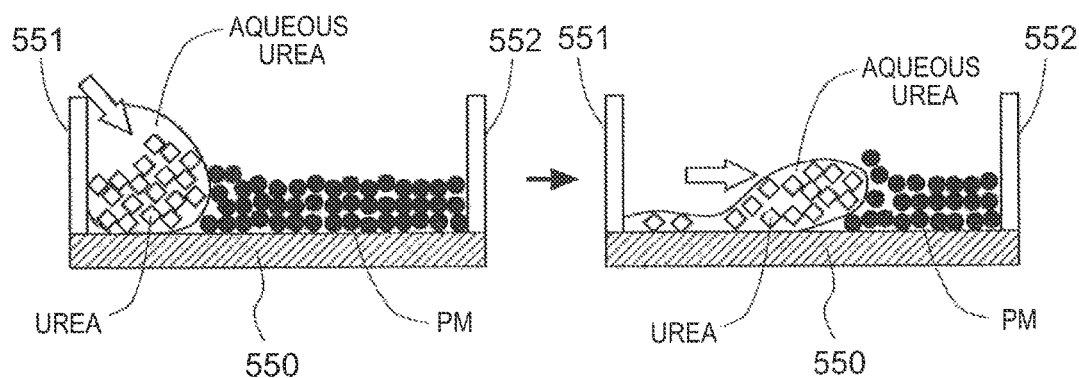
Figure 7B:
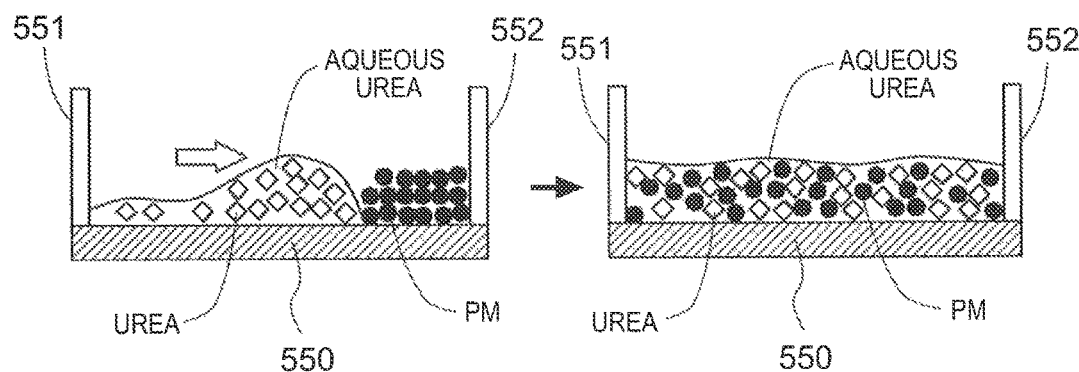
FIG. 7B is a view showing images of a portion of the PM sensor between the electrodes when the output value of the PM sensor exhibits the behavior as indicated in a portion of line L3 of FIG. 6 surrounded by broken line b.
Figure 7C:
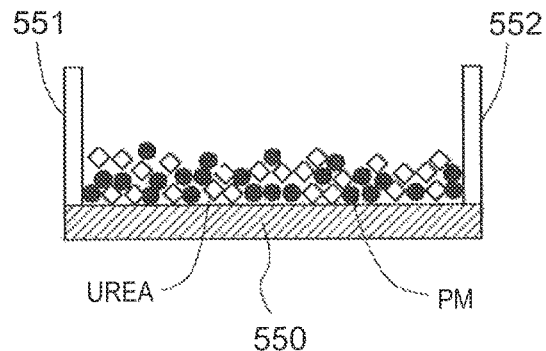
FIG. 7C is a view showing images of a portion of the PM sensor between the electrodes when the output value of the PM sensor exhibits the behavior as indicated in a portion of line L3 of FIG. 6 surrounded by broken line c.

FIG. 7A through FIG. 7C show images of conditions between the electrodes 551, 552 when aqueous urea is attached to between the electrodes 551, 552 of the PM sensor 55 in which the PM is deposited. FIG. 7A shows conditions between the electrodes 551, 552 when the output value of the PM sensor 55 behaves as indicated in a portion of line L3 of FIG. 6 surrounded by broken line a. FIG. 7B shows conditions between the electrodes 551, 552 when the output value of the PM sensor 55 behaves as indicated in a portion of line L3 of FIG. 6 surrounded by broken line b. FIG. 7C shows a condition between the electrodes 551, 552 when the output value of the PM sensor 55 behaves as indicated in a portion of line L3 of FIG. 6 surrounded by broken line c. In FIG. 7A-FIG. 7C, rhomboids represent aqueous urea, and black circles represent PM.

As described above, when there is an abnormality in the PM trapping function of the SCRF 51, the period from the voltage application time to the output start time is shortened, as compared with the case where the PM trapping function is in a normal status. Accordingly, the output start time ts3 of line L3 is earlier than the output start time ts1 of line L1. Also, the output value of the PM sensor 55 indicated by line L3 gradually increases from the output start time ts3, as the amount of PM deposited between the electrodes 551, 552 increases. At this time, if aqueous urea is attached to between the electrodes 551, 552, at a time denoted as tx, a part of PM deposited between the electrodes 551, 552 may be peeled off by the aqueous urea, as shown in FIG. 7A. In this case, the amount of PM deposited between the electrodes 551, 552 is reduced. Therefore, the output value of the PM sensor 55 is reduced, as indicated in the portion of line L3 of FIG. 6 surround by broken line a.

Then, if the condition in which a part of PM is peeled off by aqueous urea turns into a condition in which the electrodes 551, 552 are electrically conducted by aqueous urea containing PM, as shown in FIG. 7B, the output value of the PM sensor 55 increases again, as indicated in the portion of line L3 of FIG. 6 surrounded by broken line b. However, water contained in the aqueous urea attached between the electrodes 551, 552 evaporates with time. If water in aqueous urea evaporates, a mixture of PM and urea (precipitate) is deposited between the electrodes 551, 552, as shown in FIG. 7C. Here, urea has lower electric conductivity than PM. Therefore, if the mixture of PM and urea is deposited between the electrodes 551, 552, the resistance value between the electrodes 551, 552 increases, as compared with a condition in which only the PM is deposited between the electrodes 551, 552. Accordingly, after the output value of the PM sensor 55 is increased again due to electric conduction between the electrodes 551, 552 via aqueous urea containing PM, the output value decreases as water in the aqueous urea evaporates. In the condition where the mixture of PM and urea is deposited between the electrodes 551, 552, the output value of the PM sensor 55 is lower than the output value in the condition where only the same quantity of PM is deposited between the electrodes 551, 552, as indicated by the portion of line L3 of FIG. 6 surrounded by broken line c.

Since the output value of the PM sensor behaves as described above when aqueous urea is attached to between the electrodes 551, 552 of the PM sensor 55, the output value of the PM sensor 55 at the determination time td after a lapse of the predetermined determination period dtd from the voltage application time may largely deviated from a value corresponding to the integrated value of the amount of PM flowing out from the SCRF 51 during the determination period dtd. In this case, it is difficult, through the diagnosis of the PM trapping function using the output value of the PM sensor 55 at the above-described determination time td, to accurately diagnose the PM trapping function of the SCRF 51. For example, if aqueous urea is attached to between the electrodes 551, 552 of the PM sensor 55 in the timing as indicated in FIG. 6, and the PM between the electrodes 551, 552 is peeled off by the aqueous urea, the determination time td is reached at the time when the output value of the PM sensor 55 is reduced. In this case, it may be erroneously determined, in the diagnosis of the PM trapping function as described above, that the PM trapping function of the SCRF 51 is in a normal status, even though there is an abnormality in the PM trapping function of the SCRF 51. Also, in the case where the determination time td is reached when the output value of the PM sensor 55 is reduced, in the condition in which the mixture of PM and urea is deposited between the electrodes 551, 552 of the PM sensor 55, as compared with the time when the same quantity of PM alone is deposited between the electrodes 551, 552, it may be erroneously determined, in the above-described diagnosis of the PM trapping function, that the PM trapping function of the SCRF 51 is in a normal status, as in the case as described above.

Thus, in this embodiment, the diagnosis of the PM trapping function based on the output value of the PM sensor 55 at the determination time td, as described above, will be called "second diagnosis of the PM trapping function". The PM trapping function of the SCRF 51 is also diagnosed through "first diagnosis of the PM trapping function" which is conducted by a diagnostic method different from that of the second diagnosis of the PM trapping function. In the following, the first diagnosis of the PM trapping function according to this embodiment will be described.

In this embodiment, the output value of the PM sensor 55 after the voltage application time is continuously monitored by the monitoring unit 101 of the ECU 10. Namely, the behavior of the output value of the PM sensor 55 as shown in FIG. 5 or FIG. 6 can be monitored by the monitoring unit 101. In the first diagnosis of the PM trapping function, the PM trapping function of the SCRF 51 is diagnosed, based on the behavior of the output value of the PM sensor 55 until the predetermined determination period dtd elapses from the voltage application time, which behavior is monitored by the monitoring unit 101. More specifically, assuming that it is determined in the above-described diagnosis of the NOx converting function that the NOx converting function of the SCRF 51 is in a normal status, it is determined that there is an abnormality in the PM trapping function of the SCRF 51 if the output value of the PM sensor 55 is reduced before the predetermined determination period dtd elapses from the voltage application time.

The PM flowing out from the SCRF 51 is continuously trapped between the electrodes 551, 552 of the PM sensor 55. Therefore, unless aqueous urea is attached to between the electrodes 551, 552, the output value of the PM sensor 55 continuously increases in accordance with the continuous increase of the amount of PM deposited between the electrodes 551, 552, as indicated by L1, L2 in FIG. 5. On the other hand, if aqueous urea is attached to between the electrodes 551, 552, and a part of the PM deposited between the electrodes 551, 552 is peeled off by the aqueous urea, the output value of the PM sensor 55 is reduced, as indicated in the portion of line L3 of FIG. 6 surrounded by broken line a. Accordingly, if the output value of the PM sensor 55, which has continuously increased, is reduced after the voltage application time, this behavior of the output value of the PM sensor 55 is highly likely to indicate that aqueous urea is attached to between the electrodes 551, 552 of the PM sensor 55. If the NOx converting function of the SCRF 51 is in a normal status at this time, it can be determined that aqueous urea flows out from the SCRF 51 not because aqueous urea that is supposed to be consumed for reduction of NOx is not consumed for reduction of NOx, but because of a failure, such as breakage or erosion, in the SCRF 51 (namely, decline in the PM trapping function). Therefore, if the output value of the PM sensor 55 exhibits the behavior as described above when it is determined that the NOx converting function of the SCRF 51 is in a normal status, it can be determined that there is an abnormality in the PM trapping function of the SCRF 51. Namely, even in the case where it is erroneously determined that the PM trapping function is normal in the above-described second diagnosis of the PM trapping function, it can be determined, in the first diagnosis of the PM trapping function, that there is an abnormality in the PM trapping function of the SCRF 51.

Figure 8:
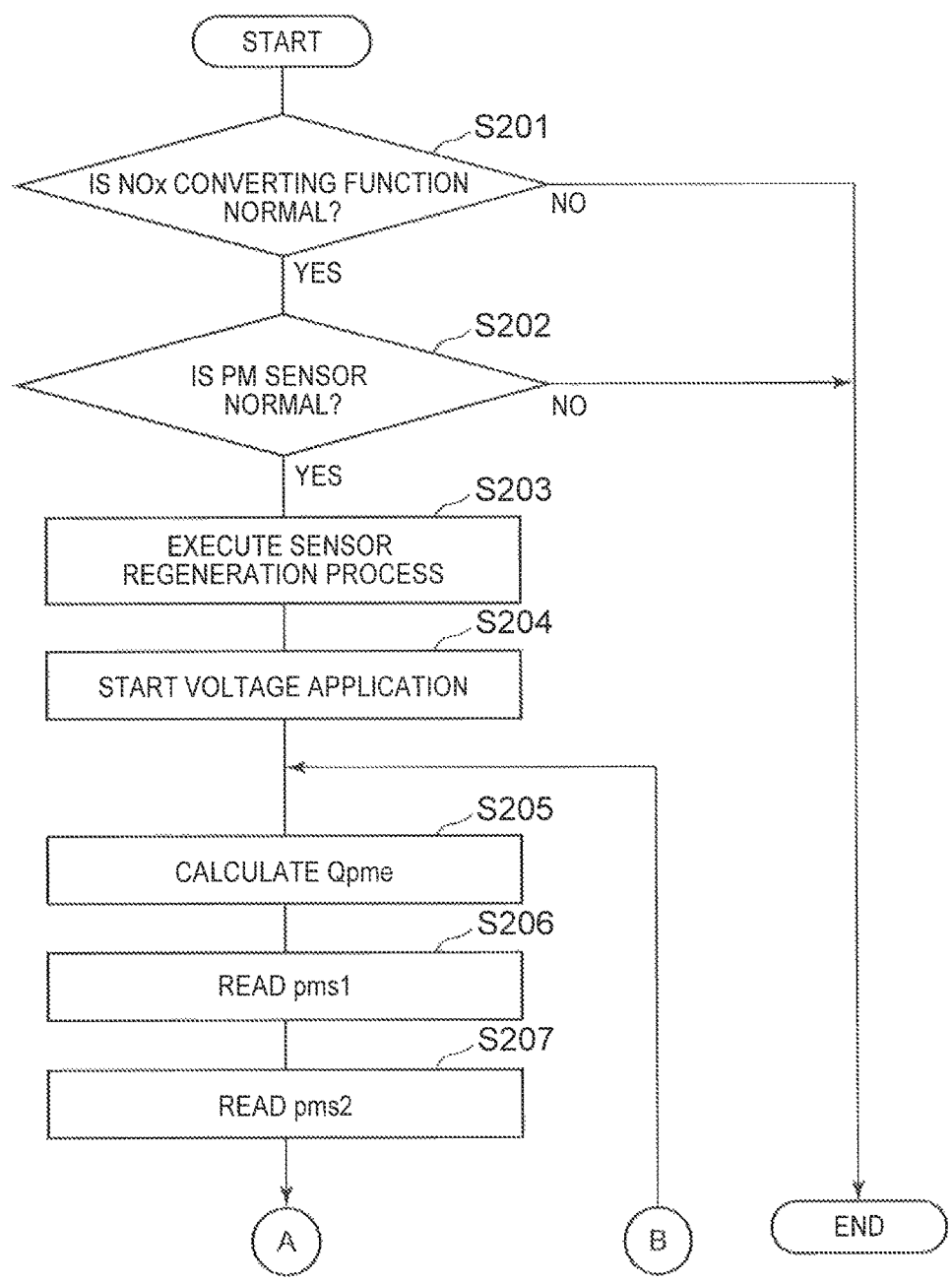
FIG. 8 is a flowchart illustrating a part of the flow of control for diagnosing the PM trapping function of the SCRF according to a disclosed embodiments.
Figure 9:
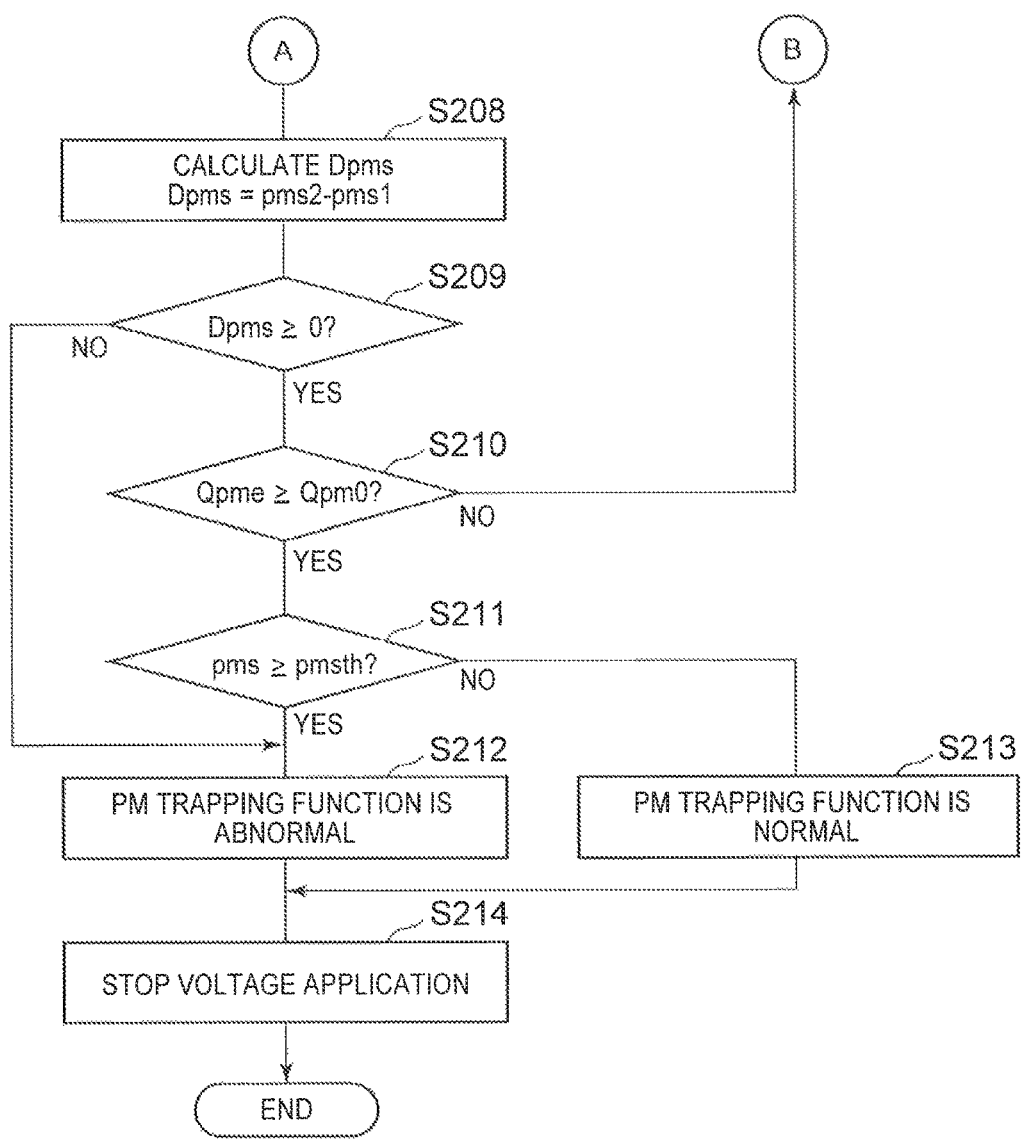
FIG. 9 is a flowchart illustrating another part of the flow of control for diagnosing the PM trapping function of the SCRF according to disclosed embodiments.

The flow of control for diagnosing the PM trapping function of the SCRF according to this embodiment will be described with reference to FIG. 8 and FIG. 9. FIG. 8 and FIG. 9 are flowcharts illustrating the flow of control for diagnosing the PM trapping function of the SCRF according to this embodiment. This flow is executed by the ECU 10 when a predetermined condition for diagnosing the PM trapping function is satisfied. The condition for diagnosing the PM trapping function is a condition under which a diagnosis of the PM trapping function of the SCRF 51 is carried out. The condition for diagnosing the PM trapping function is set so that the diagnosis of the PM trapping function of the SCRF 51 can be carried out with necessary and sufficient frequency. As one example of the condition for diagnosing the PM trapping function, the internal combustion engine 1 is in steady operation, AND a predetermined period of time has elapsed from the last execution of the flow of FIGS. 8, 9, or a predetermined period of diagnosis of the PM trapping function has elapsed since the current operation of the engine 1 was started, for example. When the PM sensor 55 is provided with a sub ECU, the flow of FIGS. 8, 9 may be executed by the sub ECU.

In the flow of FIGS. 8, 9, it is initially determined in step S201 whether the NOx converting function of the SCRF 51 is in a normal status. As described above, in this embodiment, the flow shown in FIG. 4 is executed, separately from the flow shown in FIGS. 8, 9, so as to diagnose the NOx converting function of the SCRF 51, and the result of the diagnosis is stored in the ECU 10. In step S201, the result of the diagnosis of the NOx converting function of the SCRF 51, which was conducted immediately before the flow of FIGS. 8, 9 starts being executed, is read. If the result of the diagnosis to the effect that there is an abnormality in the NOx converting function of the SCRF 51 is stored in the ECU 10, a negative decision (NO) is made in step S201. In this case, execution of this flow is terminated. On the other hand, if the result of the diagnosis to the effect that there is an abnormality in the NOx converting function of the SCRF 51 is not stored in the ECU 10, an affirmative decision (YES) is made in step S201. Namely, in this embodiment, the ECU 10 determines that the NOx converting function of the SCRF 51 is normal, based on the fact that it is not determined from the diagnosis that there is an abnormality in the NOx converting function of the SCRF 51. When an affirmative decision (YES) is made in step S201, step S202 is then executed.

The case where an abnormality already appears in the PM trapping function of the SCRF 51 at the time that the flow of control for diagnosing the NOx converting function of the SCRF 51 as shown in FIG. 4 is executed may be considered. In this case, if aqueous urea flows out from the SCRF 51, due to the abnormality in the PM trapping function of the SCRF 51, the aqueous urea that has flown out may reach the downstream NOx sensor 57. It is, however, to be noted that, even if the aqueous urea reaches the downstream NOx sensor 57, an influence of aqueous urea on the output value of the downstream NOx sensor 57 is smaller than an influence of aqueous urea on the output value of the PM sensor 55, in view of the structure of the NOx sensor. Therefore, even if aqueous urea flows out from the SCRF 51 due to an abnormality in the PM trapping function of the SCRF 51, the outflow of aqueous urea is less likely or unlikely to influence the result of diagnosis of the NOx converting function of the SCRF 51.

In step S202, it is determined whether the PM sensor 55 is in a normal condition. In this embodiment, like the diagnosis of the NOx converting function of the SCRF 51, the flow of control for diagnosing a failure of the PM sensor 55 is executed as a separate routine from the flow of FIGS. 8, 9, and the result of the diagnosis is stored in the ECU 10. In step S202, the result of failure diagnosis of the PM sensor 55 stored in the ECU 10 is read. If the diagnostic result that the PM sensor 55 is at fault is stored in the ECU 10, a negative decision (NO) is made in step S202. In this case, execution of this flow is terminated. On the other hand, if the diagnostic result that the PM sensor 55 is at fault is not stored in the ECU 10, an affirmative decision (YES) is made in step S202. In this case, step S203 is then executed. Any known method may be employed as a method of diagnosing a failure of the PM sensor 55.

In step S203, the sensor regeneration process is executed. Namely, electric power is supplied from the power supply 60 to the heater 555. Then, the temperature of the sensor element 553 is controlled to a temperature at which PM can be oxidized. In step S203, supply of electric power to the heater 555 is continued until a predetermined sensor regeneration time elapses from the start of supply of electric power. Here, the sensor regeneration time may be a fixed value that is determined in advance by experiment, or the like, as a length of time sufficient to remove PM deposited between the electrodes 551, 552 of the PM sensor 55. Also, the amount of PM deposited between the electrodes 551, 552 at the start of the sensor regeneration process may be estimated, and the sensor regeneration time may be set based on the estimated PM deposition amount. If the sensor regeneration time elapses from the start of power supply to the heater 555, supply of electric power from the power supply 60 to the heater 555 is stopped, so that execution of the sensor regeneration process is terminated. At the time when execution of the sensor regeneration process is terminated, the amount of PM deposited between the electrodes 551, 552 of the PM sensor 55 is substantially equal to zero.

Then, step S204 is executed. In step S204, a voltage starts being applied to the electrodes 551, 552 of the PM sensor 55. As a result, trapping of PM between the electrodes 551, 552 is promoted. In this embodiment, when a voltage starts being applied to the electrodes 551, 552 of the PM sensor 55, monitoring of the output value of the PM sensor 55 by the monitoring unit 101 of the ECU 10 is also started. As described above, a cooling period for cooling the electrodes 551, 552 may be provided between the time when the sensor regeneration process is completed, and the time when a voltage starts being applied to the electrodes 551, 552 of the PM sensor 55. Also, as described above, the time at which a voltage starts being applied to the electrodes 551, 552 of the PM sensor 55 may not necessarily coincide with the time at which monitoring of the output value of the PM sensor 55 by the monitoring unit 101 of the ECU 10 is started.

Then, in step S205, the reference PM deposition amount Qpme is calculated. In this step, the reference PM deposition amount Qpme is calculated, based on the operating conditions of the internal combustion engine 1, and the PM deposition amount in the filter 51 when it is assumed that the filter 51 is in the reference failed status. The PM deposition amount in the filter 51 when it is assumed that the filter 51 is in the reference failed status can be calculated by estimating the amount of PM trapped by the filter 51 when it is assumed that the filter 51 is in the reference failed status, and the amount of PM removed from the filter 51 when the PM is oxidized due to increase of the exhaust gas temperature, and integrating these estimated values.

Then, in step S206, an output value pms1 of the PM sensor 55 is read. In the following, the output value pms1 of the PM sensor 55 read in step S206 will be called "first sensor output value pms1". Then, in step S207, an output value pms2 of the PM sensor 55 after a lapse of a predetermined time from a point in time at which the first sensor output value pms1 read in step S206 was generated from the PM sensor 55 is read. In the following, the output value pms2 of the PM sensor 55 read in step S207 will be called "second sensor output value pms2".

Then, in step S208, a sensor output difference Dpms is calculated by subtracting the first sensor output value pms1 read in step S206 from the second sensor output value pms2 read in step S207. Then, in step S209, it is determined whether the sensor output difference Dpms calculated in step S208 is equal to or larger than zero. An error may be contained in the output value of the PM sensor 55. Therefore, in step S209, it may be determined whether the sensor output difference Dpms is equal to or larger than a predetermined threshold value that is larger than zero and set in view of an error in the output value of the PM sensor 55. If an affirmative decision (YES) is made in step S209, it is then determined in step S210 whether the reference PM deposition amount Qpme calculated in step S205 is equal to or larger than the criterial PM deposition amount Qpm0. If a negative decision (NO) is made in step S210, the process from step S205 to step S210 is executed again. If, on the other hand, an affirmative decision (YES) is made in step S210, it is determined that the determination period dtd has elapsed from the voltage application time, while the output value of the PM sensor 55 is not reduced during this period. In this case, in step S211, a diagnosis of the PM trapping function of the SCRF 51 based on the output value of the PM sensor 55 at the determination time td (namely, the second diagnosis of the PM trapping function) is conducted. More specifically, it is determined whether the output value pms of the PM sensor 55 at the time when the reference PM deposition amount Qpme reaches the criterial PM deposition amount Qpm0 (namely, the output value of the PM sensor 55 at the determination time td) is equal to or larger than an abnormality determination value pmsth. If an affirmative decision (YES) is made in step S211, it is then determined in step S212 that there is an abnormality in the PM trapping function of the SCRF 51. If, on the other hand, a negative decision (NO) is made in step S211, it is then determined in step S213 that there is no abnormality in the PM trapping function of the SCRF 51. Namely, it is determined that the PM trapping function of the SCRF 51 is in a normal status. After it is determined in step S212 or step S213 that the PM trapping function of the SCRF 51 is abnormal or normal, voltage application to the electrodes 551, 552 of the PM sensor 55 is stopped in step S214.

If, on the other hand, a negative decision (NO) is made in step S209, the second sensor output value pms2 is reduced to be smaller than the first sensor output value pms1, before the determination period dtd elapses from the voltage application time. Namely, the output value of the PM sensor 55 is reduced. In this case, aqueous urea is highly likely to be attached to between the electrodes 551, 552 of the PM sensor 55. Namely, it can be determined that outflow or discharge of aqueous urea from the SCRF 51 has occurred due to decline in the PM trapping function of the SCRF 51. In this case, it is then determined in step S212 that there is an abnormality in the PM trapping function of the SCRF 51.

In the flow as described above, when it is determined that the output value of the PM sensor 55 is reduced before the determination period dtd elapses from the voltage application time, it is determined at this point in time that there is an abnormality in the PM trapping function of the SCRF 51. Namely, the first diagnosis of the PM trapping function is carried out before the determination period dtd elapses from the voltage application time. However, the first diagnosis of the PM trapping function may be carried out after the determination period dtd elapses from the voltage application time. In this case, too, it is determined whether there is an abnormality in the PM trapping function of the SCRF 51, based on whether a reduction of the output value of the PM sensor 55 occurred before the determination period dtd elapses from the voltage application time. Also, in this case, if it is determined, through the first diagnosis of the PM trapping function, that there is an abnormality in the PM trapping function of the SCRF 51, the result of the first diagnosis of the PM trapping function is prioritized, even when it is determined, through the second diagnosis of the PM trapping function, that the PM trapping function of the SCRF 51 is in a normal status. Namely, it is finally determined that there is an abnormality in the PM trapping function of the SCRF 51.

In the case where a SCR catalyst and a filter are different bodies or members, and the SCR catalyst is provided upstream of the filter in the exhaust passage, as in a known emission control system, the possibility of occurrence of a failure, such as breakage or erosion, in the SCR catalyst, which failure causes outflow of aqueous urea, is lower than that of the SCRF. If the SCR catalyst normally performs the NOx converting function, aqueous urea is unlikely to flow out to the downstream side of the filter, even if the PM trapping function of the filter is deteriorated. Accordingly, if the NOx converting function of the SCR catalyst itself is in a normal status, aqueous urea may reach the PM sensor provided downstream of the filter, only in the case where the surface of the substrate of the SCR catalyst is covered with PM, and the SCR catalyst cannot perform the NOx converting function. On the other hand, in the SCRF, aqueous urea is likely to flow out due to decline in the PM trapping function, as described above. Accordingly, if an attempt to limit supply of aqueous urea to the SCRF in order to reduce an influence of aqueous urea on the output value of the PM sensor is made, in the diagnosis of the PM trapping function of the SCRF based on the output value of the PM sensor, injection of aqueous urea from the urea addition valve needs to be limited (for example, the injection amount is reduced or the injection is stopped) each time the diagnosis of the PM trapping function is conducted. However, if injection of aqueous urea is limited each time the diagnosis of the PM trapping function is conducted, the NOx conversion rate in the SCRF may be excessively reduced. On the other hand, in this embodiment, the first diagnosis of the PM trapping function is conducted, so that the PM trapping function of the SCRF 51 can be diagnosed without limiting supply of aqueous urea to the SCRF 51. Accordingly, it is possible to curb reduction of the NOx conversion rate in the SCRF 51, which would be caused by the limited injection of aqueous urea from the aqueous urea addition valve 53.

In this embodiment, the PM trapping function of the SCRF is diagnosed through the first diagnosis of the PM trapping function and the second diagnosis of the PM trapping function. However, in some embodiments, it is not always necessary to conduct the second diagnosis of the PM trapping function. If aqueous urea is injected in a condition where there is an abnormality in the PM trapping function of the SCRF, the aqueous urea is relatively highly likely to flow out from the SCRF. Accordingly, the output reduction of the PM sensor is also relatively highly likely to occur due to attachment of aqueous urea to between the electrodes. Therefore, it can be determined with some degree of accuracy whether there is an abnormality in the PM trapping function of the SCRF, only through the first diagnosis of the PM trapping function. However, if the PM trapping function of the SCRF is diagnosed through both the first diagnosis of the PM trapping function and the second diagnosis of the PM trapping function, as in this embodiment, the accuracy in the diagnosis can be further enhanced.

In some embodiments, the PM trapping function of the SCRF 51 is diagnosed in substantially the same manner as discussed above. In some embodiments, when it is determined, in the first diagnosis of the PM trapping function, that there is an abnormality in the PM trapping function of the SCRF 51, this result of diagnosis is treated as a temporary diagnostic result. Then, when the temporary diagnostic result is obtained, the sensor regeneration process and the voltage application to the electrodes 551, 552 of the PM sensor 55 are carried out again, in a condition where injection of aqueous urea from the aqueous urea addition valve 53 is stopped, and the second diagnosis of the PM trapping function is conducted.

In the above manner, the PM trapping function of the SCRF 51 is diagnosed, based on the output value of the PM sensor 55 at the time when the predetermined determination period dtd has elapsed from the voltage application time, under a condition where injection of aqueous urea from the aqueous urea addition valve 53 is stopped. Namely, the second diagnosis of the PM trapping function can be conducted in a condition where an influence of aqueous urea on the output value of the PM sensor 55 is eliminated. Therefore, the PM trapping function of the SCRF 51 can be diagnosed with higher accuracy. Also, injection of aqueous urea from the aqueous urea addition valve 53 is stopped only when the temporary diagnostic result that there is an abnormality in the PM trapping function of the SCRF 51 is obtained through the first diagnosis of the PM trapping function. In this manner, the frequency of execution of the operation to stop injection of aqueous urea can be reduced, as compared with the case where injection of aqueous urea from the aqueous urea addition valve 53 is stopped each time the PM trapping function of the SCR 51 is diagnosed based on the output value of the PM sensor 55. Accordingly, it is possible to curb reduction of the NOx conversion rate in the SCRF 51 caused by stopping of injection of aqueous urea.

Figure 10:
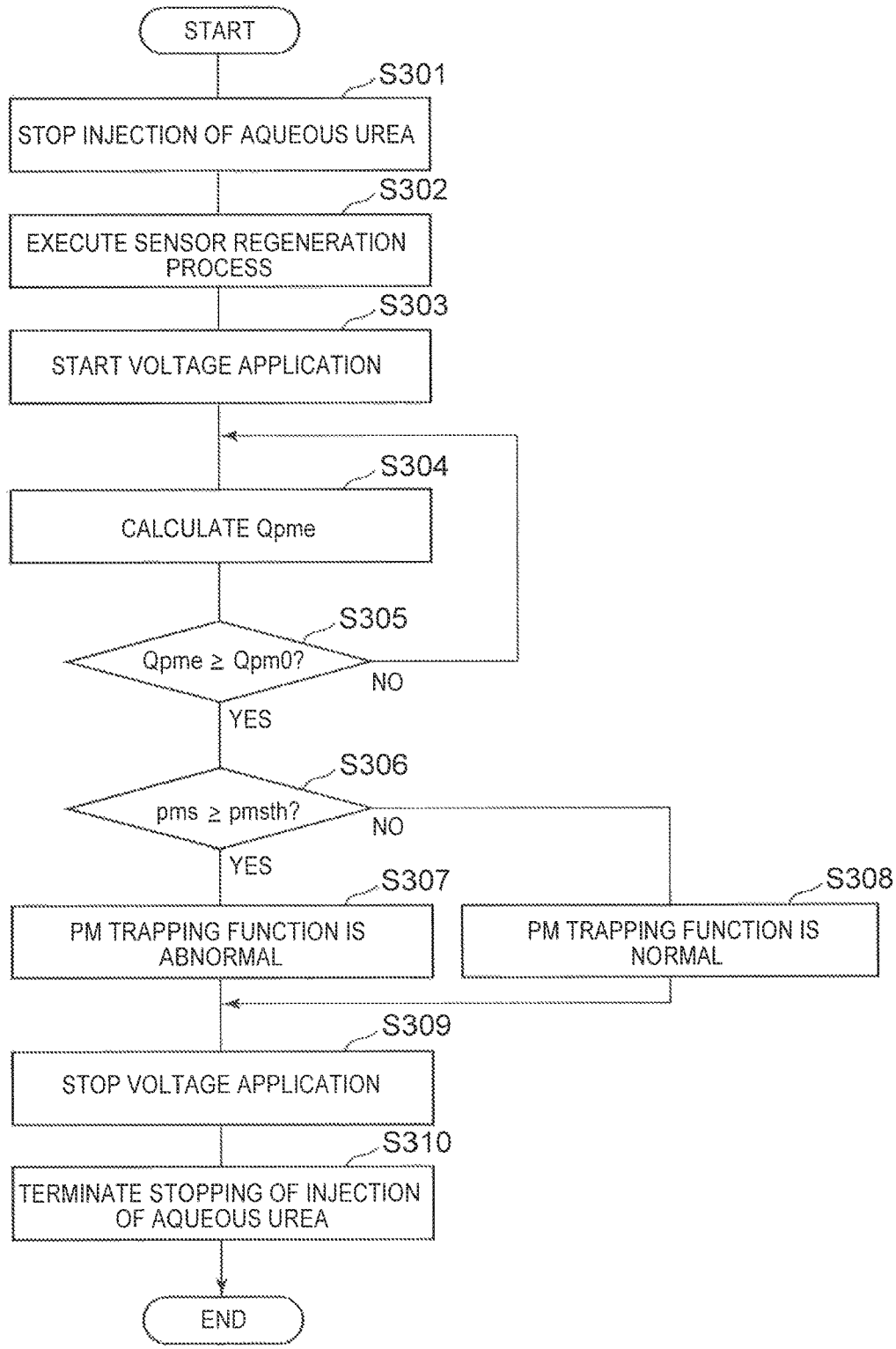
FIG. 10 is a flowchart illustrating a part of the flow of control for diagnosing the PM trapping function of the SCRF according to disclosed embodiments.

The flow of control for diagnosing the PM trapping function of the SCRF according to this embodiment will be described with reference to FIG. 10. FIG. 10 is a flowchart illustrating the flow of control for diagnosing the PM trapping function of the SCRF according to this embodiment. In this embodiment, too, the flow of control for diagnosing the PM trapping function of the SCRF as shown in FIGS. 8, 9 is executed. When a negative decision (NO) is made in step S209 in the flow of control for diagnosing the PM trapping function of the SCRF as shown in FIGS. 8, 9, and it is determined in step S212 that there is an abnormality in the PM trapping function of the SCRF 51, the flow shown in FIG. 10 is executed by the ECU 10, after voltage application to the electrodes 551, 552 is stopped in step S214. If the PM sensor 55 is provided with a sub ECU, the flow of FIG. 10 may be executed by the sub ECU, like the flow shown in FIGS. 8, 9.

In the flow of FIG. 10, injection of aqueous urea from the aqueous urea addition valve 53 is initially stopped in step S301. Then, the same operations as those of steps S203 and S204 of the flow shown in FIGS. 8, 9 are performed in steps S302 and S303, respectively. Namely, the sensor regeneration process is performed, and a voltage starts being applied to the electrodes 551, 552 of the PM sensor 55 after completion of the sensor regeneration process. Then, the same operations as those of steps S205 and S210 of the flow shown in FIGS. 8, 9 are performed in steps S304 and S305, respectively. Namely, the reference PM deposition amount Qpme is calculated, and then, it is determined whether the calculated reference PM deposition amount Qpme is equal to or larger than the criterial PM deposition amount Qpm0. If a negative decision (NO) is made in step S305, steps S304 and S305 are executed again. If, on the other hand, an affirmative decision (YES) is made in step S305, step S306 is then executed.

In step S306, it is determined whether the output value pms of the PM sensor 55 obtained when the reference PM deposition amount Qpme reaches the criterial PM deposition amount Qpm0 is equal to or larger than the abnormality determination value pmsth, as in step S211 of the flow shown in FIGS. 8, 9. Namely, the second diagnosis of the PM trapping function is conducted. If an affirmative decision (YES) is made in step S306, it is then determined in step S307 that there is an abnormality in the PM trapping function of the SCRF 51, as in step S212 of the flow shown in FIGS. 8, 9. If, on the other hand, a negative decision (NO) is made in step S306, it is then determined in step S308 that the PM trapping function of the SCRF 51 is in a normal status, as in step S213 of the flow shown in FIGS. 8, 9. After it is determined in step S307 or S308 that the PM trapping function of the SCRF 51 is abnormal or normal, voltage application to the electrodes 551, 552 of the PM sensor 55 is stopped in step S309, as in step S214 of the flow shown in FIGS. 8, 9. Then, in step S310, the operation to stop injection of aqueous urea from the aqueous urea addition valve 53 is terminated.

In the embodiment as described above, when the temporary diagnostic result that there is an abnormality in the PM trapping function of the SCRF 51 is obtained through the first diagnosis of the PM trapping function, injection of aqueous urea from the aqueous urea addition valve 53 is stopped. However, it is not always necessary to stop injection of aqueous urea from the aqueous urea addition valve 53, but an influence of aqueous urea on the output value of the PM sensor 55 may be reduced by limiting supply of aqueous urea to the SCRF 51. As a result, the PM trapping function of the SCRF 51 can be diagnosed with higher accuracy. Accordingly, in this embodiment, when the temporary diagnostic result that there is an abnormality in the PM trapping function of the SCRF 51 is obtained through the first diagnosis of the PM trapping function, the sensor regeneration process and voltage application to the electrodes 551, 552 of the PM sensor 55 may be performed again, in a condition where the amount of aqueous urea injected from the aqueous urea addition valve 53 is reduced, and then the second diagnosis of the PM trapping function may be conducted.

Also, in this embodiment, when the temporary diagnostic result that there is an abnormality in the PM trapping function of the SCRF 51 is obtained through the first diagnosis of the PM trapping function, injection of aqueous urea from the aqueous urea addition valve 53 is stopped, and then, the sensor regeneration process starts being executed. However, in order to eliminate or reduce the influence of aqueous urea on the output value of the PM sensor 55, it is only required to limit injection of aqueous urea from the aqueous urea addition valve 53 by the time when deposition of the PM between the electrodes 551, 552 of the PM sensor 55 is restarted. Accordingly, in the case of this embodiment, injection of aqueous urea from the aqueous urea addition valve 53 is continued as usual during execution of the sensor regeneration process, and injection of aqueous urea may be stopped or the amount of aqueous urea injected may be reduced from the voltage application time.

Figure 11:
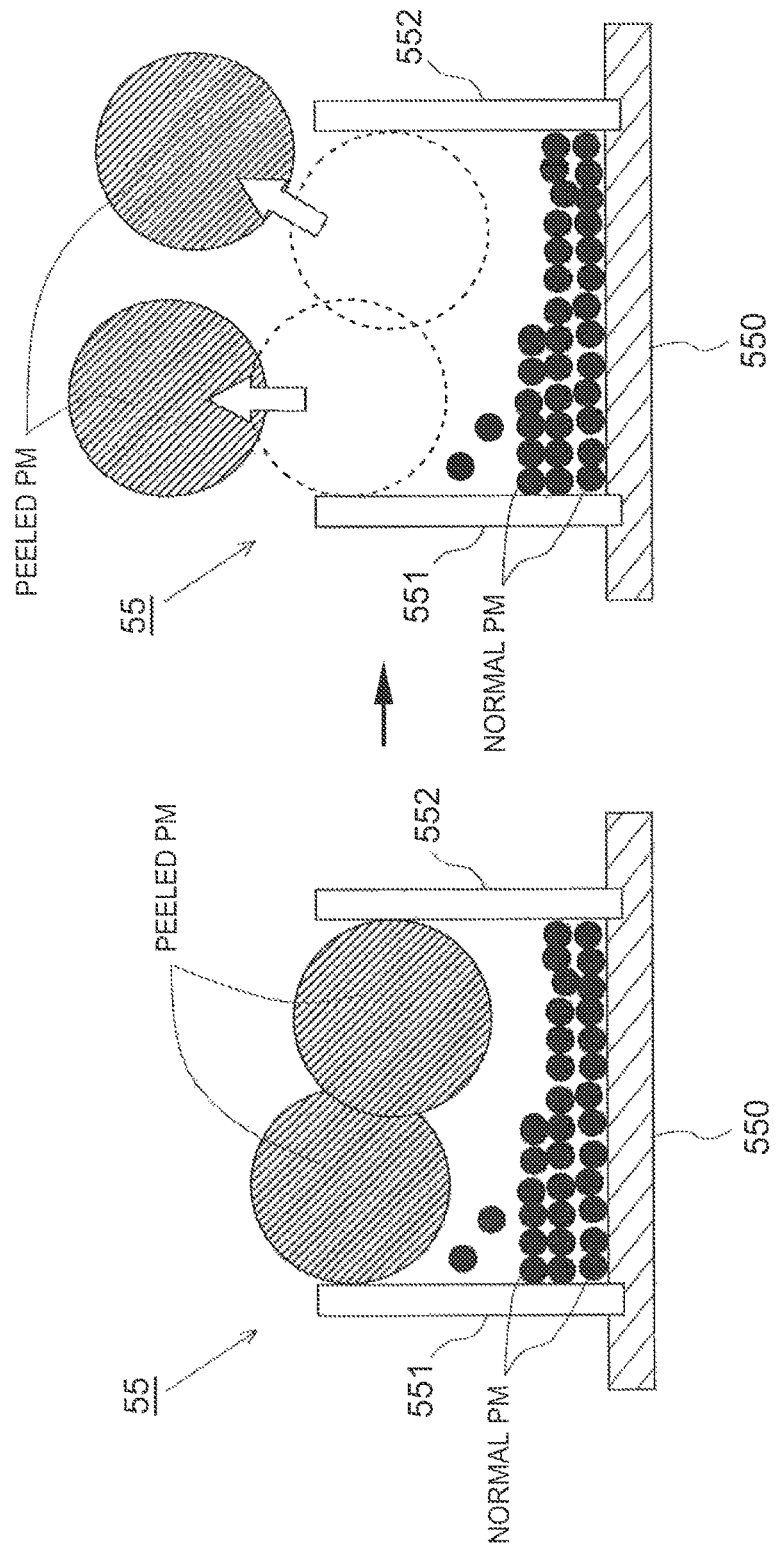
FIG. 11 is a view showing images of PM deposited between the electrodes of the PM sensor.

In some embodiments, an influence of peeled PM on the output value of the PM sensor 55 is taken into consideration, in the diagnosis of the PM trapping function of the SCRF 51. In the arrangement of the exhaust system of the internal combustion engine shown in FIG. 1, a part of PM in exhaust gas is attached to a wall of the exhaust passage 5, and structures of the exhaust system, such as a downstream end face of the filter 51 and the oxidation catalyst 50. The PM once attached to the wall of the exhaust passage 5 and the exhaust-system structures may be peeled off from the wall and the exhaust-system structures, and the PM thus peeled off may reach the PM sensor 55 and may be trapped between the electrodes 551, 552. In the following, an influence of the peeled PM on the output value of the PM sensor 55 when this phenomenon takes place will be described with reference to FIG. 11. FIG. 11 shows images of PM deposited between the electrodes 551, 552 of the PM sensor 55. The left-side view of FIG. 11 shows a condition in which the peeled PM, in addition to normal PM contained in exhaust gas discharged from the engine 1, is trapped between the electrodes 551, 552, so that the peeled PM and normal PM are deposited between the electrodes 551, 552. On the other hand, the right-side view of FIG. 11 shows a condition in which the peeled PM, which was once trapped between the electrodes 551, 552, is removed from between the electrodes 551, 552.

If the PM is attached to the wall of the exhaust passage 5 and the exhaust-system structures, the PM is deposited and condensed on the wall and the exhaust-system structures. The condensed PM is then peeled off, to produce "peeled PM". Therefore, the size of the peeled PM is usually larger than that of the normal PM. Thus, if the peeled PM is trapped between the electrodes 551, 552 of the PM sensor 55, as shown in FIG. 11, the amount of PM deposited between the electrodes 551, 552 rapidly increases, as compared with the time when only the normal PM is trapped between the electrodes 551, 552 of the PM sensor 55. As a result, the output value of the PM sensor 55 rapidly increases. However, the peeled PM, whose size is larger than that of the normal PM, is more likely to be removed from between the electrodes 551, 552 of the PM sensor 55 than the normal PM. When the peeled PM, which was once trapped between the electrodes 551, 552 of the PM sensor 55, is removed from between the electrodes 551, 552, the output value of the PM sensor 55, which has increased due to the increase of the PM deposition amount, is reduced. Namely, when peeled PM is generated and trapped between the electrodes 551, 552 of the PM sensor 55, during a period from the voltage application time to the time when the determination period dtd elapses, the output value of the PM sensor 55 may be reduced even if the PM trapping function of the SCRF 51 is in a normal status. If the reduction of the output value of the PM sensor 55 due to the peeled PM is confused with reduction of the output value of the PM sensor 55 due to aqueous urea, in the first diagnosis of the PM trapping function, it may be erroneously determined that there is an abnormality in the PM trapping function of the SCRF 51, even though the PM trapping function of the SCRF 51 is actually in a normal status.

Thus, in this embodiment, when a predetermined peeled PM generation condition as a condition under which peeled PM can be generated is satisfied, the diagnosis of the PM trapping function of the SCRF 51 based on the output value of the PM sensor 55 is not conducted. In other words, the PM trapping function of the SCRF 51 is diagnosed, based on the output value of the PM sensor 55 obtained when it is determined that the NOx converting function of the SCRF 51 is in a normal status, and the peeled PM generation condition is not satisfied. With this arrangement, it is less likely or unlikely to be erroneously determined that there is an abnormality in the PM trapping function of the SCRF 51, because of an influence of the peeled PM, even though the PM trapping function of the SCRF 51 is actually in a normal status. Accordingly, the PM trapping function of the SCRF 51 is diagnosed with further improved accuracy.

In this connection, the peeled PM is more likely to be generated as the amount of PM deposited on the wall of the exhaust passage 5 and the exhaust-system structures increases. Also, if the above-described filter regeneration process is performed, the temperature of exhaust gas flowing in the exhaust passage 5 rises, so that not only the PM deposited in the SCRF 51 but also the PM attached to the wall of the exhaust passage 5 and the exhaust-system structures is highly likely to be oxidized and removed. After execution of the filter regeneration process is finished, the PM starts being attached again to the wall of the exhaust passage 5 and the exhaust-system structures, as PM is discharged from the internal combustion engine 1. Therefore, the amount of PM deposited on the wall of the exhaust passage 5 and the exhaust-system structures has a correlation with the integrated value of the PM discharge amount (the integrated value of PM discharged from the engine 1, from the time when execution of the filter regeneration process is finished). Also, as the flow rate of exhaust gas flowing in the exhaust passage 5 is larger, the PM once deposited on the wall of the exhaust passage 5 and the exhaust-system structures is more likely to be peeled off. Namely, as the flow rate of exhaust gas flowing in the exhaust passage 5 is larger, the peeled PM is more likely to be generated. Thus, in this embodiment, it is determined whether the peeled PM generation condition is satisfied, using the integrated value of the PM discharge amount and the flow rate of exhaust gas as parameters.

Figure 12:
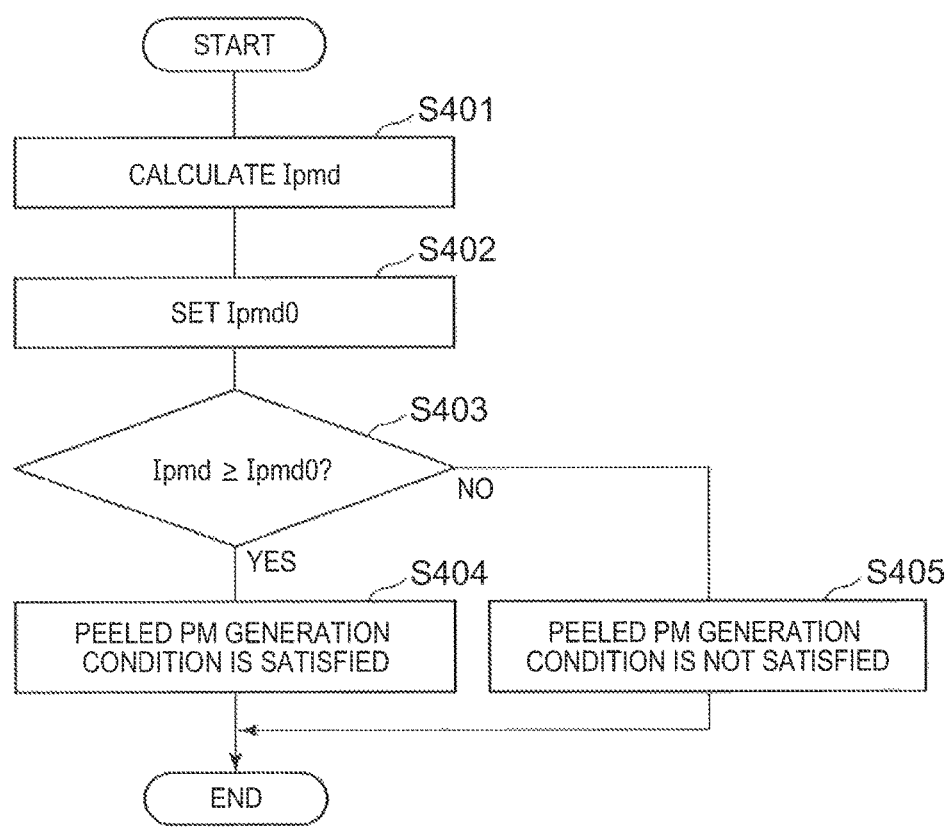
FIG. 12 is a flowchart illustrating the flow of control for determining whether a peeled PM generation condition is satisfied according to disclosed embodiments.

The flow of control for determining whether the peeled PM generation condition is satisfied according to this embodiment will be described with reference to FIG. 12. FIG. 12 is a flowchart illustrating the flow of control for determining whether the peeled PM generation condition is satisfied, according to this embodiment. The flow of FIG. 12 is stored in advance in the ECU 10, and is repeatedly executed by the ECU 10 at given intervals, during operation of the internal combustion engine 1.

In the flow of FIG. 12, initially in step S401, the integrated value Ipmd of the PM discharge amount after completion of the last filter regeneration process (namely, after fuel injection from the fuel addition valve 52 for the above-described filter regeneration process is stopped) is calculated. The amount of PM discharged from the internal combustion engine 1 may be estimated based on the operating conditions of the engine 1. Then, in step S402, a criterial integrated value Ipmd0 as a threshold value used for determining whether the peeled PM generation condition is satisfied is set based on the flow rate of exhaust gas. At this time, the criterial integrated value Ipmd0 is set to a smaller value as the flow rate of exhaust gas is larger. The flow rate of exhaust gas may be estimated based on the output value of the air flow meter 40. Also, the relationship between the criterial integrated value Ipmd0 and the flow rate of exhaust gas is determined in advance by experiment, or the like. This relationship is stored as a map or a function in the ECU 10. In step S402, the criterial integrated value Ipmd0 is set using this map or function.

Then, it is determined in step S403 whether the integrated value Ipmd of the PM discharge amount calculated in step S401 is equal to or larger than the criterial integrated value Ipmd0 set in step S402. If an affirmative decision (YES) is made in step S402, namely, if the integrated value Ipmd of the PM discharge amount is equal to or larger than the criterial integrated value Ipmd0, it is then determined in step S404 that the peeled PM generation condition is satisfied. If, on the other hand, a negative decision (NO) is made in step S402, namely, if the integrated value Ipmd of the PM discharge amount is smaller than the criterial integrated value Ipmd0, it is then determined in step S405 that the peeled PM generation condition is not satisfied. Then, the result of determination obtained in step S404 or S405 is stored in the ECU 10.

Figure 13:
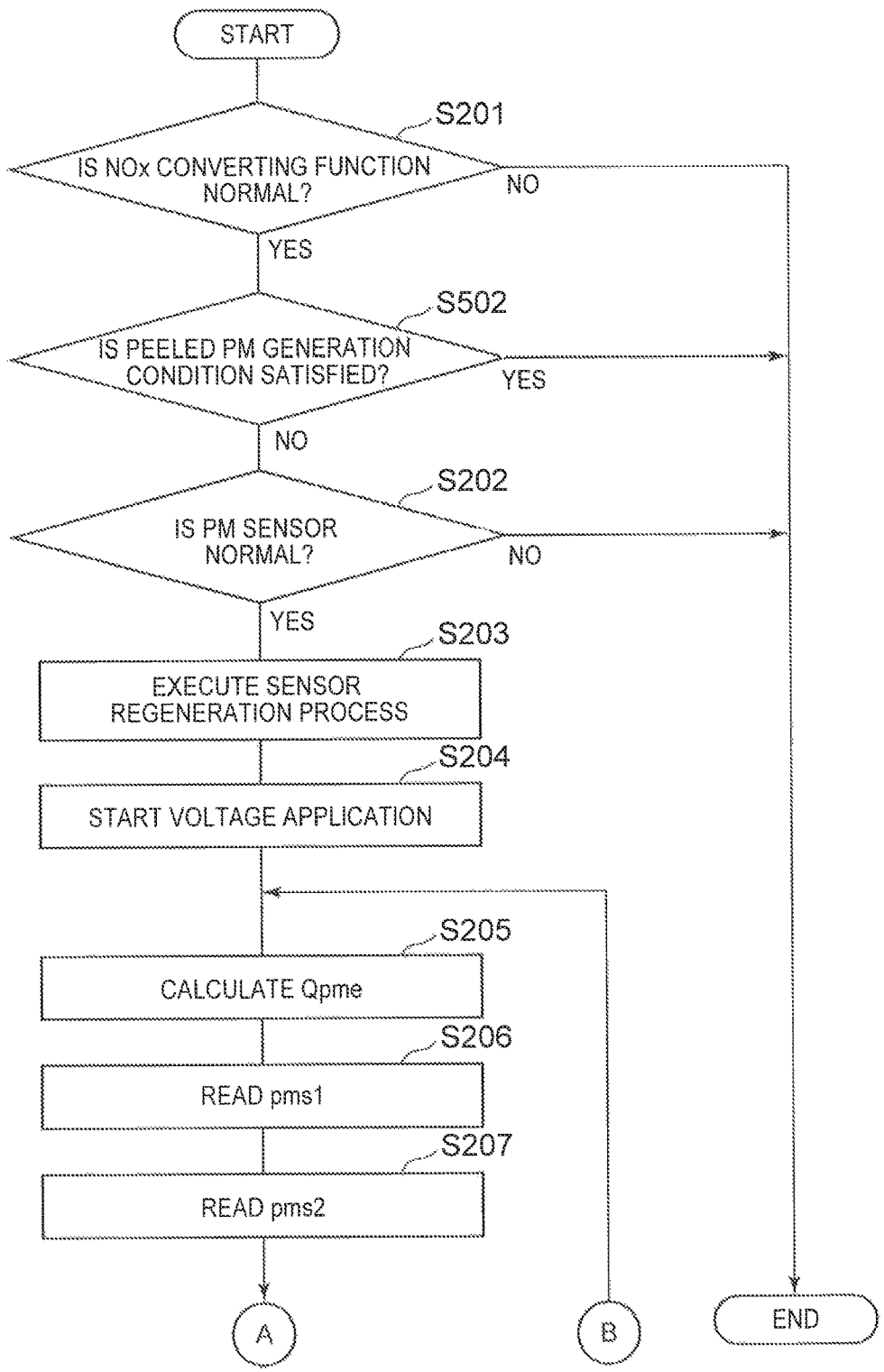
FIG. 13 is a flowchart illustrating a part of the flow of control for diagnosing the PM trapping function of the SCRF according to disclosed embodiments.

Next, the flow of control for diagnosing the PM trapping function of the SCRF according to this embodiment will be described with reference to FIG. 13. FIG. 13 is a flowchart illustrating a part of the flow of control for diagnosing the PM trapping function of the SCRF according to this embodiment. The flow of FIG. 13 is executed in the same timing as that of the flow of control for diagnosing the PM trapping function of the SCRF as shown in FIGS. 8 and 9. Also, the operation performed in each of steps other than step S502 in the flow of FIG. 13 is substantially the same as the operation performed in each of the corresponding steps in the flow shown in FIGS. 8, 9. Therefore, the same reference numerals are assigned to the steps in which the same operations as those of the steps in the flow shown in FIGS. 8, 9 are performed, and explanation of these steps will not be provided.

In the flow of FIG. 13, if an affirmative decision (YES) is made in step S201, namely, if it is determined that the NOx converting function of the SCRF 51 is in a normal status, step S502 is then executed. In step S502, it is determined whether the peeled PM generation condition is satisfied. As described above, in this embodiment, the flow shown in FIG. 12 is executed, so that it is determined whether the peeled PM generation condition is satisfied, and the result of the determination is stored in the ECU 10. In step S502, the determination result stored in the ECU 10 is read. Then, if the determination result that the peeled PM generation condition is satisfied is stored in the ECU 10, an affirmative decision (YES) is made in step 502. In this case, execution of the flow shown in FIG. 13 is terminated. If, on the other hand, the determination result that the peeled PM generation condition is not satisfied is stored in the ECU 10, a negative decision (NO) is made in step S502. In this case, step S202 is then executed. Step S202 and subsequent steps are identical with those of the flow shown in FIGS. 8, 9.

In this embodiment, it is determined whether the peeled PM generation condition is satisfied, using the integrated value of the PM discharge amount and the flow rate of exhaust gas as parameters, as described above. However, both the integrated value of the PM discharge amount and the flow rate of exhaust gas are not necessarily used as the parameters for determining whether the peeled PM generation condition is satisfied, but only the integrated value of the PM discharge amount may be used. It is, however, to be noted that the use of both of the integrated value of the PM discharge amount and the flow rate of exhaust gas makes it possible to determine, with higher accuracy, whether the peeled PM generation condition is satisfied, as compared with the case where only the integrated value of the PM discharge amount is used. Also, it may be determined whether the peeled PM generation condition is satisfied, using a parameter or parameters correlated with the possibility of generation of peeled PM, other than the integrated value of the PM discharge amount and the flow rate of the exhaust gas. For example, it may be more simply determined whether a peeled PM generation condition is satisfied, based on the travelling distance of the vehicle on which the engine 1 is installed, as measured from a point in time at which execution of the filter regeneration process is finished.

In this embodiment, the flow of control for determining whether the peeled PM generation condition is satisfied, as shown in FIG. 12, is provided separately from the flow of control for diagnosing the PM trapping function of the SCRF as shown in FIG. 13. However, the steps in the flow shown in FIG. 12 may be incorporated into the flow shown in FIG. 13. In this case, steps S401 to S403 shown in FIG. 12 are executed, in place of step S502, in the flow shown in FIG. 13. Namely, when an affirmative decision (YES) is made in step S201 of the flow shown in FIG. 13, steps S401 to S403 shown in FIG. 12 are then executed. Then, if an affirmative decision (YES) is made in step S403, execution of the flow shown in FIG. 13 is terminated. If, on the other hand, a negative decision (NO) is made in step S403, step S202 is then executed.

The disclosed embodiments as described above may be combined with each other. For example, when it is determined that there is an abnormality in the PM trapping function of the SCRF 51, through the first diagnosis of the PM trapping function conducted when the peeled PM generation condition is not satisfied, this determination may be treated as a temporary diagnostic result. When this temporary diagnostic result is obtained, the sensor regeneration process and the voltage application to the electrodes 551, 552 of the PM sensor 55 may be carried out again, in a condition where injection of aqueous urea from the aqueous urea addition valve 53 is stopped (or the amount of aqueous urea injected is reduced), and then the second diagnosis of the PM trapping function may be conducted.

What is claimed is:

1. A system for an internal combustion engine, the system comprising:
    a filter provided in an exhaust passage of the internal combustion engine, the filter supporting a selective reduction NOx catalyst that reduces NOx in exhaust gas using ammonia as a reducing agent, the filter being configured to trap particulate matter (PM) contained in the exhaust gas;
    an aqueous urea addition device located upstream of the filter in the exhaust passage, the aqueous urea addition device being configured to inject aqueous urea into the exhaust gas;
    a PM sensor provided downstream of the filter in the exhaust passage, the PM sensor having a pair of electrodes, the PM sensor being configured to output a signal corresponding to a deposition amount of the PM when the PM is deposited between the pair of electrodes and the pair of electrodes conduct electricity; and
    an electronic control unit programmed to:
    calculate a NOx conversion rate in the filter;
    determine whether a NOx converting function of the filter is normal, based on the NOx conversion rate;
    execute a sensor regeneration process for removing the PM deposited between the electrodes of the PM sensor;
    continuously monitor an output value of the PM sensor after a predetermined PM deposition restart time, after execution of the sensor regeneration process is finished, the PM deposition restart time being a point in time at which deposition of the PM between the electrodes of the PM sensor is supposed to be restarted;

determine that there is an abnormality in a PM trapping function of the filter, when the output value of the PM sensor, which has been continuously monitored, is reduced when the electronic control unit determines that the NOx converting function of the filter is in a normal status, wherein when the output value of the PM sensor, which has been continuously monitored, is reduced when the electronic control unit determines that the NOx converting function of the filter is in the normal status, the electronic control unit is programmed to limit injection of aqueous urea from the aqueous urea addition device after the PM deposition restart time, and diagnose the PM trapping function of the filter based on the output value of the PM sensor at a time when a predetermined determination period elapses from the PM deposition restart time; and wherein the electronic control unit is programmed to limit injection of aqueous urea from the aqueous urea addition device after the PM deposition restart time only when the electronic control unit determines that there is the abnormality in the PM trapping function of the filter in response to the output value of the PM sensor, which has been continuously monitored, being reduced while the electronic control unit determines that the NOx converting function of the filter is in the normal state.

2. The system according to claim 1, wherein
when the output value of the PM sensor, which has been continuously monitored, is not reduced when the electronic control unit determines that the NOx converting function of the filter is in the normal status, the electronic control unit is programmed to diagnose the PM trapping function of the filter, based on the output value of the PM sensor at a time when a predetermined determination period elapses from the PM deposition restart time.

3. A system for an internal combustion engine, the system comprising:
a filter provided in an exhaust passage of the internal combustion engine, the filter supporting a selective reduction NOx catalyst that reduces NOx in exhaust gas using ammonia as a reducing agent, the filter being configured to trap particulate matter (PM) contained in the exhaust gas;
an aqueous urea addition device located upstream of the filter in the exhaust passage, the aqueous urea addition device being configured to inject aqueous urea into the exhaust gas;
a PM sensor provided downstream of the filter in the exhaust passage, the PM sensor having a pair of electrodes, the PM sensor being configured to output a signal corresponding to a deposition amount of the PM when the PM is deposited between the pair of electrodes and the pair of electrodes conduct electricity; and
an electronic control unit programmed to:
calculate a NOx conversion rate in the filter;
determine whether a NOx converting function of the filter is normal, based on the NOx conversion rate;
execute a sensor regeneration process for removing the PM deposited between the electrodes of the PM sensor;
continuously monitor an output value of the PM sensor after a predetermined PM deposition restart time, after execution of the sensor regeneration process is finished, the PM deposition restart time being a point in time at which deposition of the PM between the electrodes of the PM sensor is supposed to be restarted; and
determine that there is an abnormality in a PM trapping function of the filter, when the output value of the PM sensor, which has been continuously monitored, is reduced when the electronic control unit determines that the NOx converting function of the filter is in a normal status, wherein the electronic control unit is programmed to determine whether a predetermined peeled PM generation condition is satisfied, the peeled PM generation condition being a condition under which a phenomenon that the PM once attached to a wall of the exhaust passage or an exhaust-system structure is peeled off from the wall of the exhaust passage or the exhaust-system structure can occur,
the electronic control unit is programmed to diagnose the PM trapping function of the filter, based on the output value of the PM sensor which has been continuously monitored, when the electronic control unit determines that the NOx converting function of the filter is in the normal status, and the electronic control unit determines that the peeled PM generation condition is not satisfied; and
wherein the electronic control unit is programmed to limit injection of aqueous urea from the aqueous urea addition device after the PM deposition restart time only when the electronic control unit determines that there is the abnormality in the PM trapping function of the filter in response to the output value of the PM sensor, which has been continuously monitored, being reduced while the electronic control unit determines that the NOx converting function of the filter is in the normal state.

4. The system according to claim 3, wherein
the electronic control unit is programmed to control the internal combustion engine such that a filter regeneration process for oxidizing and removing the PM deposited in the filter is executed; and
the electronic control unit is programmed to determine whether the peeled PM generation condition is satisfied, based on an integrated value of an amount of PM discharged from the internal combustion engine after completion of the filter regeneration process.

5. The system according to claim 4, wherein
the electronic control unit is programmed to determine whether the peeled PM generation condition is satisfied, based on a flow rate of exhaust gas flowing in the exhaust passage, in addition to the integrated value of the amount of PM discharged from the internal combustion engine after completion of the filter regeneration process.

* * * * *